(12) United States Patent
Tsai et al.

(10) Patent No.: US 8,101,387 B2
(45) Date of Patent: Jan. 24, 2012

(54) PROCESS TO SEQUENCE BIOREACTOR MODULES FOR SERIAL GAS FLOW AND UNIFORM GAS VELOCITY

(75) Inventors: Shih-Perng Tsai, Naperville, IL (US); Seong-Hoon Yoon, Naperville, IL (US); Rahul Basu, Naperville, IL (US)

(73) Assignee: Coskata, Inc., Warrenville, IL (US)

( * ) Notice: Subject to any disclaimer, the term of this patent is extended or adjusted under 35 U.S.C. 154(b) by 562 days.

(21) Appl. No.: 12/258,204

(22) Filed: Oct. 24, 2008

(65) Prior Publication Data

US 2009/0104676 A1    Apr. 23, 2009

Related U.S. Application Data

(63) Continuation of application No. 11/781,717, filed on Jul. 23, 2007, now abandoned, and a continuation of application No. 12/036,007, filed on Feb. 22, 2008.

(51) Int. Cl.
| | |
|---|---|
| *C12P 7/54* | (2006.01) |
| *C12P 7/52* | (2006.01) |
| *C12P 7/04* | (2006.01) |
| *C12P 7/16* | (2006.01) |
| *C12P 7/06* | (2006.01) |

(52) U.S. Cl. ........ 435/140; 435/141; 435/157; 435/160; 435/161

(58) Field of Classification Search .................. 435/140, 435/141, 157, 160, 161
See application file for complete search history.

(56) References Cited

U.S. PATENT DOCUMENTS

| | | | |
|---|---|---|---|
| 4,181,604 | A | 1/1980 | Onishi et al. |
| 4,442,206 | A | 4/1984 | Michaels et al. |
| 4,746,435 | A | 5/1988 | Onishi et al. |
| 5,106,506 | A | 4/1992 | Schmidt et al. |
| 5,173,429 | A | 12/1992 | Gaddy et al. |
| 5,753,474 | A | 5/1998 | Ramey |
| 6,043,392 | A | 3/2000 | Holtzapple et al. |
| 6,136,577 | A | 10/2000 | Gaddy |
| 6,340,581 | B1 | 1/2002 | Gaddy |
| 6,387,262 | B1 | 5/2002 | Rittmann et al. |
| 6,558,549 | B2 | 5/2003 | Cote et al. |
| 6,908,547 | B2 | 6/2005 | Cote et al. |
| 6,919,488 | B2 | 7/2005 | Melnichuk et al. |
| 7,083,956 | B2 | 8/2006 | Paterek |
| 7,118,672 | B2 | 10/2006 | Husain et al. |
| 7,169,295 | B2 | 1/2007 | Husain et al. |
| 7,189,323 | B2 | 3/2007 | Lofqvist et al. |
| 7,285,402 | B2 | 10/2007 | Gaddy et al. |
| 2004/0211723 | A1 | 10/2004 | Husain et al. |
| 2005/0009159 | A1 | 1/2005 | Paterek |
| 2005/0054087 | A1 | 3/2005 | Cote et al. |
| 2006/0021936 | A1 | 2/2006 | Husain et al. |
| 2006/0037896 | A1 | 2/2006 | Cote et al. |
| 2006/0163157 | A1 | 7/2006 | Cote et al. |
| 2009/0035848 | A1 | 2/2009 | Hickey et al. |
| 2009/0215139 | A1 | 8/2009 | Datta et al. |

FOREIGN PATENT DOCUMENTS

| | | |
|---|---|---|
| WO | WO0208438 | 1/2002 |
| WO | WO0208438 A2 | 1/2002 |
| WO | WO2008154301 | 12/2008 |

OTHER PUBLICATIONS

U.S. Appl. No. 11/441,392, filed May 25, 2006, Tanner et al.
U.S. Appl. No. 11/514,385, filed Aug. 31, 2006, Hickey.
U.S. Appl. No. 12/036,007, filed Feb. 22, 2008, Tsai et al.
U.S. Appl. No. 12/258,180, filed Oct. 24, 2008, Tsai et al.
U.S. Appl. No. 12/123,249, filed May 19, 2008, Hickey et al.
U.S. Appl. No. 12/111,734, filed Apr. 29, 2008, Tsai et al.
U.S. Appl. No. 12/258,162, filed Oct. 24, 2008, Tsai et al.
U.S. Appl. No. 11/972,454, filed Jan. 10, 2008, Hickey et al.
U.S. Appl. No. 11/781,717, filed Jul. 23, 2007, Hickey et al.
Popular Mechanics, Coskata Ethanol Technology—How it Works—Illustration and Analysis, http://www.popularmechanics.com/science/research/4248759.html?series=19, Feb. 22, 2008, pp. 1-3.
Ethanol Production by *Saccharomyces cerevisiae*Immobilized in Hollow-Fiber Membrane Bioreactors, Douglas S. Inloes, et al., Applied and Environmental Microbiology, Jul. 1983, pp. 264-278, vol. 46. No. 1.
"Evidence for Production of n-Butanol from Carbon Monoxide by *Butyribacterium methylotrophicum*," Journal of Fermentation and Bioengineering, vol. 72, 1991, p. 58-60.
"Production of butanol and ethanol from synthesis gas via fermentation," FUEL, vol. 70, May 1991, p. 615-619.
Das, A. and L.G. Ljungdahl, Electron Transport Systems in Acetogens, Chapter 14, in Biochemistry and Physiology of Anaerobic Bacteria, L.G. Ljungdahl et al eds., Springer (2003).
Drake, H.L.and K. Kusel, Diverse Physiologic Potential of Acetogens, Chapter 13, in Biochemistry and Physiology of Anaerobic Bacteria, L.G. Ljungdahl et al eds., Springer (2003).
Muller, V., Minireview: Energy Conservation in Acetogenic Bacteria, Applied and Environmental Microbiology, vol. 69, 11, 6345-53, Nov. 2003.
Rahtin Datta and J.G. Zeikus, Anaerobic Conversion of One-Carbon Compounds. vol. 24 of Developments in Industrial Microbiology, 1983.
Datta et al, Reprinted from vol. 24 of Developments in Industrial Microbilogy, a Publication of the Society for Industrial Microbiology—1985, Chapter 10, Anaerobic Bioconversion of One-Carbon Compounds, pp. 1-6.

(Continued)

Primary Examiner — Herbert J Lilling

(57) ABSTRACT

This invention is a process for managing the gas flow through a plurality of bioconversion modules that provide a gas liquid interface. The conversion modules provide the gas liquid interface across an activated surface that converts at least some of the gas components into desired liquid products. Arrangement of the modules and control of gas flow in accordance with this invention enhances the utilization of the gas and the production of desired liquid products by adjusting the flow area to compensate for changes in the volume of the feed gas. Improved control of the gas velocity through the bioconversion modules eliminates problems of liquid condensation and flow maldistribution. The process may sequence the modules to mitigate time variation in microorganism activity and incorporate additional periodic process steps.

14 Claims, 13 Drawing Sheets

OTHER PUBLICATIONS

Kim et al, Plant Cell Immobilization in a Dual Hollow Fiber Bioreactor, Biotechnology Techniques vol. 3 No. 2, 1989, pp. 139-144, Received as revised Jan. 30.

Nloes, D. S. et al, Ethanol Production by Saccharomyces cerevisiae Immobilized in Hollow-Fiber Membrane Bioreactors, Received Apr. 11, 1983/Accepted Apr. 25, 1983, Applied and Environmental Microbiology, Jul. 1983, vol. 46. No. 1, pp. 264-278.

Henstra, A. M. et al, Microbiology of Synthesis Gas Fermentation for Biofuel Production, ScienceDirect, Current Opinion in Biotechnology 2007, 18:200-206.

U.S. Appl. No. 12/258,193, filed Oct. 24, 2008, Datta et al.

Clausen, E.C., et al, "Ethanol From Biomass by Gasification/Fermentation", Presented at Plastics, Tires, Auto Wastes/Biomass MSW Symposium, Fall 1993, Chicago, 38 (3).

Klasson, K.T., et al., "Biological Production of Liquid and Gaseous Fuels from Synthesis Gas," Appl. Biochem. Biotechnol., vol. 24-25, No. 1, Mar. 1990, 857-873.

Vega, J. L., et al., "The Biological Production of Ethanol from Synthesis Gas," Appl. Biochem. Biotechnol. vol. 20-21, No. 1, Jan. 1989, 781-797.

Phillips, John R., et al., "Synthesis Gas as Substrate for the Biological Production of Fuels and Chemicals," Appl. Biochem. Biotechnol. vol. 45-46, No. 1, Mar. 1994, 145-157.

Barik, S., et al., "Biological Production of Alcohols from Coal Through Indirect Liquefaction," Appl. Biochem. Biotechnol. vol. 18, No. 1, Aug. 1988, 363-387.

Henstra, A.M. et al. Current Opinion in Biotechnology (2007). vol. 18, pp. 200-206.

PCT/US2009/061705 International Preliminary Report on Patentability, May 5, 2011.

U.S. Appl. No. 12/581,193, filed Oct. 24, 2008, Rathin Datta.

PROCESS TO SEQUENCE BIOREACTOR MODULES FOR SERIAL GAS FLOW AND UNIFORM GAS VELOCITY

CROSS REFERENCE TO RELATED APPLICATIONS

This application claims priority from U.S. patent application Ser. No. 11/781,717, filed Jul. 23, 2007 now abandoned, and U.S. patent application Ser. No. 12/036,007, filed Feb. 22, 2008 both of which are incorporated herein in their entirety by reference.

FIELD OF THE INVENTION

This invention relates to the conversion of gas streams into liquid products using conversion modules that define separate gas and liquid contacting surfaces.

DETAILED DESCRIPTION

Background

A number of processes maintain a permeable barrier between a gas phase and a liquid phase to keep the phase separate while promoting conversion of the liquid phase or gas phase components. Many devices and equipment are used for gas transfer to microorganisms in fermentation and waste treatment applications. Most of these process use some form of membrane to provide limited contact between the gas and liquid phases.

Particular forms of membranes have found use in supporting specific types microorganisms for wastewater treatment and fermentation processes. U.S. Pat. No. 4,181,604 discloses the use of hollow fiber membranes for waste treatment where the outer surface of the fibers supports a layer of microorganisms for aerobic digestion of suspended sludge from the liquid phase.

Bioreactors constitute a class of conversion zones where cell retention by formation of biofilms provides a very good and often inexpensive way to increase the density of microorganisms in bioreactors. The membrane offers a solid matrix with large surface area for an activated surface comprising the cells that colonize and form a biofilm to contain the metabolizing cells in a matrix of biopolymers that the cells generate.

Copending U.S. patent application Ser. No. 11/781,717, filed Jul. 23, 2007 discloses a system of hollow fiber membranes for contacting syngas components such as CO or a mixture of $CO_2$ and $H_2$ with a surface of a membrane and transferring these components in contact with a biofilm on the opposite side of the membrane to provide a stable system for producing liquid products such as ethanol, butanol, hexanol and other chemicals. This membrane supported bioreactor system converts the syngas components using anaerobic microoganisms supported on the surface of membrane in the liquid phase.

The system uses microporous membranes or non-porous membranes or membranes having similar properties that transfer (dissolve) gases into liquids while concurrently serving as the support upon which the fermenting cells grow as a biofilm in a concentrated layer. Liquid is passed in the liquid side of the membranes via pumping, stirring or similar means to remove the ethanol and other soluble products formed; the products are recovered via a variety of suitable methods. The system appears best suited to maintain the liquid phase on the outside of the hollow fibers and the gas phase inside the fiber lumens.

Another form of conversion system can use asymmetric membranes. These membranes are known for use in a variety of membrane separations processes such as ultra and nano filtration. Asymmetric membranes are typically hydrophilic and have a relatively tight semi permeable "skin" layer on one side supported on a porous polymer layer. U.S. Pat. Nos. 4,442,206 and 4,440,853 show the use of the polymer layer in an asymmetric membrane to immobilize microorganisms for certain biological processes that use soluble carbon sources.

Copending U.S. patent application Ser. No. 12/036,007, filed Feb. 22, 2008 disclose the adaptation and use of such asymmetric membranes for the anaerobic bioconversion of syngas to liquids has not been shown in the past. An asymmetric membrane when used to contain anaerobic microorganisms for converting gas phase components to liquid phase components will provide a stable system for enhancing the production of liquid products. A porous side of the asymmetric membrane, referred to as a bio-layer provides pores that promote and control the growth of microorganism colonies therein while also exposing a surface over which to directly feed the microorganisms with syngas. Simultaneously another layer of the asymmetric membrane having less permeability than the bio-layer, referred to as a hydration layer, permeates liquid from the opposite side of the asymmetric membrane. In operation with syngas CO or a mixture of $CO2$ and H2 contact one side of the asymmetric membrane through the bio-layer while a nutrient and product containing liquid contacts the other through the hydration layer. When using hollow fibers the asymmetric membrane system finds greatest advantage when the gas phase contacts the outer surface of the membrane and the liquid phase passes through the lumens.

These conversion processes commonly arrange the contact surfaces in a module form. Modules typically employ a membrane to provide the contact surface. Flat sheet, spiral wound, and hollow fiber represent the most typical forms of module construction.

In the production of liquid products these conversion processes will consume a portion of the gas stream as passes through the conversion modules. Consumption of the gas reduces its volume from the time it enters until the time it leaves individual modules. As the original gas stream passes serially through a plurality of modules the reduction of volumetric gas flow rate will reduce the gas velocity through the gas flow area of similarly constructed modules. For example in a bioconversion process for the production of ethanol passage of a syngas feed through group of modules may reduce its volume by anywhere from 30% to 80% overall. Reduced gas velocity through the gas flow area in downstream modules can lead to poor contacting conditions, reduced gas conversion rates and condensation of liquids therein.

Condensation of liquids on membrane surfaces can occur in any type of membrane contacting arrangement where there is an at least partial gas phase and the suitable conditions exist. Liquid accumulation can alter flow patterns and inhibit gas transfer properties across the membrane thereby reducing the productivity and selectivity of such systems. Excess liquid formation can pose problems on any type of membrane system. When the feed syngas contains moisture, condensation of water can occur at the microorganism/gas interface as consumption of syngas results in supersaturation of water. Even when the feed syngas is undersaturated with moisture, the syngas can become saturated with moisture very soon after entering the module due to diffusion of water molecules from the liquid side to the gas side, resulting in supersaturation and condensation downstream within the module. The most severe problems occur where the condensation occurs in narrow channels. Accordingly membranes geometries such as spiral wound configuration and hollow fibers may prove most problematic when liquid accumulates in narrow gas channels or the lumens of hollow fibers.

As the gas stream passes through the conversion modules, consumption of the gas components results in changes in the gas composition along the direction of the gas flow. However, in steady state operations microorganisms at a given location are exposed to an approximately constant gas composition. Prolonged exposure to a certain gas composition can have adverse effects on the cellular viability or metabolic regulation. For example, long-term exposure to the entering gas rich in some gas components can potentially lead to excessive cell growth or preferential consumption of one gas component over the other (i.e., imbalanced gas uptake), whereas long-term exposure to the lean exiting gas can lead to starvation and cell death.

It would be desirable to have a modular membrane supported bioreactor and method of use that would overcome the above disadvantages.

SUMMARY OF THE INVENTION

This invention is a process for managing the gas flow through a plurality of conversion modules that provide a gas liquid interface by maintaining a constant gas velocity across the gas contact surface. The conversion modules provide the gas liquid interface across an activated surface that converts at least some of the gas components into desired liquid products. The gas velocity is maintained at relatively uniform conditions as the gas feed gets consumed in a series a modules by adjusting the arrangement of the modules or the intermediate addition of gas between modules. Arrangement of the modules and control of gas flow in accordance with this invention enhances the utilization of the gas and the production of desired liquid products.

In one form of the invention feed gas passes serially through multiple groups of the conversion modules and the number of conversion modules in each group declines as the gas passes from initial to the final groups of modules. Accordingly, the initial group of modules provides the greatest gas flow area for the highest volume of gas that enters the process. Each subsequent group of modules defines a smaller gas flow area to compensate for the consumption of gas in the upstream group of modules. The gas flow area declines so that each group of modules in the series has a relatively constant volumetric gas flow rate in each module and gas velocity on its collective gas contacting side. In this manner the feed gas undergoes essentially plug flow through the series of modules.

One of the simplest methods of practicing this invention reduces the gas flow area by using a plurality of modules of the same size and configuration in stages of serial flow. This method maintains a more uniform gas velocity through the modules by reducing the number of modules in each stage in proportion to the volumetric flow through the stages in the series.

Alternatively the module configuration or the number of modules may remain the same as gasses passes serially through the modules and additional gas may enter downstream stream modules to offset the upstream consumption of gas. Additional gas may comprise additional feed gas or displacement gas. While this method can provide more uniform gas flow this method does cause the additional portion of the feed gas to pass through less gas contacting surface and have a lower conversion than the original feed gas.

In either case the gas flow through the stages will vary within a predetermined range. In accordance with this invention the gas flow rate between modules in the series of stages will not vary by more than 30% and usually less than 20%, and more preferably by less than 10%. Ideally the volumetric rate between modules in the stages should remain essentially constant and vary by no more than 5%.

Essentially all of the feed gas that exits an upstream group of modules will typically pass to an adjacent group of modules. Passing essentially all of the gas from one group of the modules to the next directly downstream group of modules means passing at least 90 wt % of the effluent gas and more preferably at least 95 wt % of the gas to the next modules.

The modules also include a liquid phase that flows as a liquid media in a separate liquid flow area separated from the gas flow area. The liquid media will at minimum recover the liquid products produced by the conversion process from the feed gas by transport from the liquid flow area. The liquid media may also provide additional, catalysts, reactants or consumables to the conversion process. For example in bioconversion processes the liquid media may also supply nutrients to the microorganisms.

Any number of serial stages containing the modules may be used in the process. Use of the process only requires a minimum of two modules, however most applications will contain at least a first, last and intermediate stage of modules in the process.

The invention can apply to any conversion process that uses a series of modules to convert gas into liquid products across a gas-liquid phase partition. The most typical form of partition will comprise microporous membranes or non-porous membranes or membranes having similar properties that transfer (dissolve) gases into liquids for delivering the gas components.

The modules may configure the gas flow area and liquid flow area into any suitable geometry. The membrane configurations of flat sheets, spiral windings and hollow fibers are all acceptable.

In another form the invention may use valves or other flow controllers to periodically sequence the function or grouping of the modules so that modules alternate position with respect to the gas flow. Therefore modules may switch from receiving the entering gas flow to receiving an intermediate gas flow between modules and finally the gas flow before it exits the process. Sequencing in this manner proves most useful when the process includes a periodic regenerating or purging of selected modules. In such systems the sequencing of the module position with respect to gas flow can allow the entering gas or the exiting gas to contact the modules that most recently underwent regeneration or purging.

Preferably the process converts syngas using a microorganism that converts CO and/or a mixture of $CO_2$ and $H_2$ into ethanol and other soluble products. In such a case a membranes can serve as the support upon which the fermenting cells grow as a biofilm and are thus retained in a concentrated layer. The syngas can either contact the microorganisms directly in a biolayer or diffuse through the membrane from the gas side and into a biofilm where it is transformed by the microbes to the soluble product of interest. Liquid may pass to the liquid side of the membranes via pumping, stirring or similar means to remove the ethanol and other soluble products formed; the products are recovered via a variety of suitable methods.

Modules containing microorganisms routinely undergo a purging to remove dead cells. The type of purge depends on the phase location of the microorganisms. Where retained in the liquid phase the most effective purging technique for the microorganisms may comprise a gentle and continual agitation to wash away dead cells and other biological debris without a wholesale dislodging of the biofilm itself. When the module retains microorganisms on the gas side of the membrane the most effective purging may comprise periodically seeping liquid from the liquid contacting side of the membrane to the gas side of the membrane to create a small outwash of liquid through the layer of microorganisms.

Accordingly in one embodiment this invention is a process for the production of liquid product or products from a gas feed by its partial consumption as it passes serially through a plurality of conversion modules. A first feed gas passes in parallel flow at a first volumetric rate to a group of first modules that define a first gas flow area and a first gas flow velocity into a first gas flow area defined at least in part by a first gas contact surface of the first modules to convert a portion of the gas feed to first liquid product(s). A first stream of liquid media passes to a first liquid contact surface of said first group of modules to recover the liquid product(s) from the liquid contact surface. At least a portion of first effluent gas recovered from the first gas flow area passes at a second volumetric rate to a group of second modules that define a second gas flow area defined at least in part by a second gas contact surface of the second modules to convert a portion of the first effluent gas to more liquid product(s). The second volumetric rate is less than the first volumetric rate and the first gas flow velocity varies by no more than 30% from the second gas flow velocity. A second stream of liquid media passes to a second liquid contact surface of said second group of modules to recover the liquid product(s) from the second liquid contact surface.

In another embodiment the invention comprises a process for the production of liquid products from a gas feed by its partial consumption as it passes serially through groups of conversion modules. A feed gas passes in parallel flow at a first volumetric rate and a first gas flow velocity to a first group of modules comprising membrane elements that each define a uniform gas flow area to collectively provide a first gas flow area for contacting the feed gas with a gas contact surface therein to convert a portion of the gas feed to liquid product(s). A first stream of liquid media passes to a first liquid contact surface defined by the membrane elements of the first group of modules to recover the liquid products from the liquid contact surface. The remainder of feed gas is recovered from the first gas flow area as a first effluent gas. At least a portion of the first effluent gas passes at a second volumetric flow rate and a second flow velocity to a group of second modules comprising membrane elements wherein each module defines the same uniform gas flow area as each module in the first group of modules to collectively provide a second gas flow area for contacting the feed gas with a gas contact surface. The contacting converts an additional portion of the feed gas to more liquid product(s). In the process the first group of modules contains more modules than the second group and the second volumetric rate is less than the first volumetric rate. A second stream of liquid media passes to a liquid contact surface defined by the membrane elements of the second group of modules to recover liquid product(s) from the second liquid contact surface.

In another embodiment the invention is a process for the production of liquid products from a gas feed by its partial consumption as it passes in parallel through the individual modules within groups of bioconversion modules and serially between groups of bioconversion modules wherein the bioconversion modules comprise membrane elements that each define a uniform gas flow area, a liquid contact surface and a gas contact surface that retains a biolayer of microorganisms.

In the process a feed gas passes at a first volumetric rate to a first group of modules to collectively provide a first gas flow area and to convert a portion of the gas feed to liquid product(s). A first stream of liquid media passes to a liquid contact surface defined by said first group of modules to recover the liquid product(s) from the liquid contact surface. The remainder of feed gas gets recovered from the first gas flow area and at least a portion of the feed gas recovered from the first gas flow area passes at a second volumetric flow rate to a group of second modules to collectively provide a second gas flow area for contacting the feed gas with a gas contact surface therein to convert an additional portion of the feed gas to more liquid product(s). The second group of modules contains less modules than the first group of modules and the second volumetric rate is less than the first volumetric rate. A second stream of liquid media passes to a liquid contact surface defined by the membrane elements of the second group of modules to recover liquid product(s) from the second liquid contact surface. The remainder of the feed gas is recovered from the second gas flow area. The process periodically maintains at least one module in a purge mode by permeating the liquid media from the liquid contact surface to the gas contact surface of the module in purge mode to flush microorganisms from the module's gas contact surface and sequentially changes the module that is in purge mode so that periodically all of the modules undergo purging.

The process can apply to any number of modules and groups of modules. Each group of modules can comprises multiple banks of modules or multiple vessels containing multiple groups of modules. The only requirement for the practice of the invention is that such groups of modules have an arrangement for serial flow of gas through at least a portion of the modules in each group of modules thereby creating a decreasing gas flow area in the direction of gas flow. Separate groups of modules may be established in any manner that where the modules receive gas from a common gas distribution point and deliver gas to a common gas collection point.

All of the gas flow in a group of modules need not pass in parallel through all of the modules. The requirement for parallel flow in each group of modules stems from the desire to limit the total volumetric loss of feed gas within groups of modules. Therefore, including one or more subgroups of modules in serial flow may increase the number of modules within a group of modules provided the total variation in gas flow through a group of modules does not create flow distribution and condensation problems of the type described above within a group of modules.

BRIEF DESCRIPTION OF THE DRAWINGS

FIG. 1A is a first step in the schematic drawing;
FIG. 1B is a second step in the schematic drawing;
FIG. 1C is a third step in the schematic drawing;
FIG. 1D is a fourth step in the schematic drawing.

DETAILED DESCRIPTION OF THE INVENTION

Figure 1:
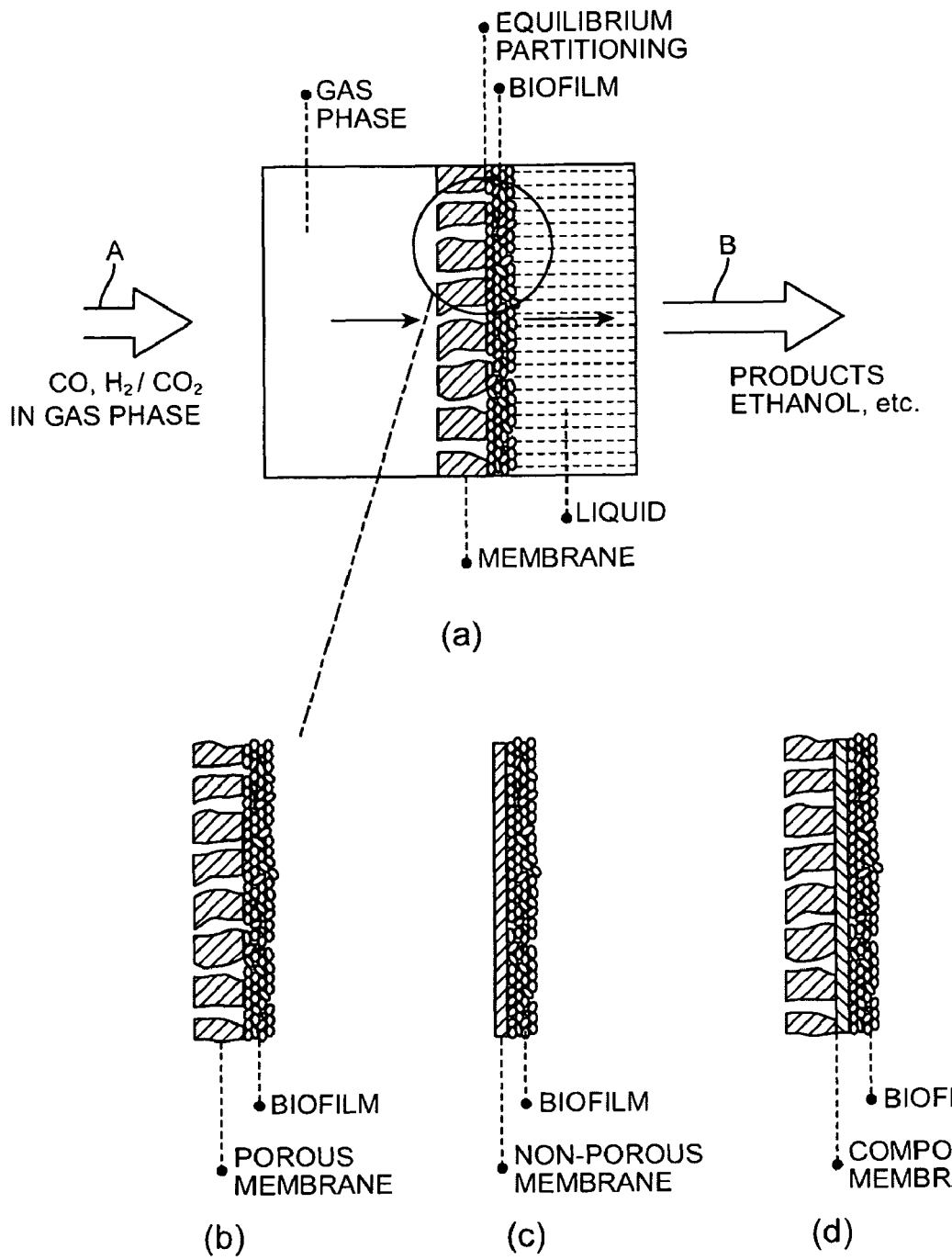
FIG. 1 is a schematic drawing showing gas diffusing through a porous membrane into a liquid and details of a porous membrane, non-porous membrane and composite membrane.

The instant invention uses microporous membranes or non-porous membranes or membranes having similar properties to fix microorganisms for contact with both a feed gas stream containing feed materials for consumption by the microorganisms and a liquid medium that serves the dual function of providing water and nutrients to the microorganisms and transporting liquid products from the microorganisms for recovery. Functionally, the membrane establishes an interface between separate gas and liquid phases while permitting limited transfer of gas and/or liquid across the interface.

These membrane arrangements take two basic forms. In one form the membrane retains the microorganisms on the face of the membrane that contacts the liquid phase, typically as a biofilm. This arrangement submerges the exterior of the membrane elements containing the microorganisms in the liquid medium and for that reason may be termed a submerged configuration. In the other form, the membrane retains the microorganisms on the face that contacts the gas phase and may do so in relatively large pore openings that become filled with microorganisms to provide a surface comprising biopores.

In the submerged configuration the process must transfer (dissolve) gases into liquids for delivering the feed gas components in the syngas directly to the cells that use them, for example CO and $H_2$ in the gas that the microorganisms transform into ethanol and other soluble products. The membranes concurrently serve as the support upon which the fermenting cells grow as a biofilm and are thus retained in a concentrated layer. This process results in highly efficient and economical transfer of the syngas at essentially 100% dissolution and utilization wherein the gas diffuses through the membrane from the gas side and into the biofilm and gets transformed by the microbes to the soluble product of interest. Liquid is passed in the liquid side of the membranes via pumping, stirring or similar means to remove the ethanol and other soluble products formed; the products are recovered via a variety of suitable methods.

In the membrane arrangements where the gas side of the membrane retains the microorganisms, the membrane usually comprises an asymmetric membrane. A porous side of the asymmetric membrane, referred to herein as a bio-layer provides pores that promote and control the growth of microorganism colonies therein while also exposing a surface over which to directly feed the microorganisms with syngas. Simultaneously another layer of the asymmetric membrane having less permeability than the bio-layer, herein referred to as a hydration layer, permeates liquid from the opposite side of the asymmetric membrane. Thus this type of arrangement uses an asymmetric membrane to provide a multi-layer membrane structure having a highly porous bio-layer for retaining the microorganisms within its pores and one or more hydration layers for controlling the supply of water to and from the bio-layer. In its operation gas contacts one side of the asymmetric membrane through the bio-layer while a nutrient and product containing liquid contacts the other through the hydration layer. Either the bio-layer or hydration layer may comprise multiple layers. The bio-layer, the hydration layer and/or additional layers may also serve to occlude pore openings, extract products, and supply moisture and nutrients within the bioreactor system.

When used to contain anaerobic microorganisms for converting syngas (herein defined to include any gas containing CO and/or a mixture of $CO_2$ and $H_2$ as its principal components) the system operates in a highly efficient and economical manner to transfer of the syngas at essentially 100% utilization. Thus, the asymmetric membrane can provide an important component of a fermentor configuration for enhancing the production of liquid products such as ethanol, butanol, hexanol, and other chemicals from a syngas stream. During syngas fermentation with the asymmetric membrane carbon monoxide or hydrogen/carbon dioxide from the syngas diffuses into the bio-layer in the porous membrane wall and is converted by the immobilized microorganisms into ethanol or other water-soluble products, which is then diffused into the aqueous stream flowing over the hydration layer and carried out of the bioreactor. The immobilized microorganisms remain hydrated through contact with the aqueous stream that passes through the hydration layer.

The asymmetric membrane locates one or more less porous hydration layers opposite the gas contacting side establish an interface to provide water and trace nutrients that travel from the liquid toward the contained microorganisms while simultaneously extracting liquid products from the microorganisms. The extracted liquid flows across the hydration layer and into the liquid medium. Thus the desired products and the syngas from which they are produced flow through the layers of the membrane in the same direction, from the highly porous bio-layer to the less porous hydration layer. The liquid that contacts the less porous layer circulates over the membrane's liquid contacting surface and out of the bioreactor to facilities for the removal of the desired products.

The bio-pores of the bio-layer retain microorganisms for the production of the products from the syngas. The bio-layer keeps the microorganisms concentrated in bio-pores while still in direct contact with the syngas through a gas contacting side of bio-layer thereby keeping syngas components readily available to enhance production of ethanol and other soluble products by the retained microorganisms. The microorganisms may reside in the bio-layer in isolation or as a biofilm. Some protrusion of the microorganisms outside of the biopores and past the gas contacting surface will not stop the operation of the bioreactor system. However, the thickness of the bio-layer will dictate the thickness of any biofilm or colony of microorganisms so that the microorganisms fill up the bio-pores to the surface level of the bio-layer's gas contacting side. This permits pre-engineering of the microorganisms into a layer with a thickness that matches the thickness of the bio-layer wall. It also provides the added advantage of keeping microorganisms well confined and preventing their catastrophic loss.

Placing the hydration layer between the microorganisms and the liquid simplifies the operation of downstream separation facilities. The hydration layer provides a substantial barrier between the microorganisms and the product containing liquid that keeps the liquid flowing to separation facilities free of microorganisms and other biological contaminants. Eliminating biological contaminants from the liquid effluent removes the need for filtering and/or recycling of such materials.

Where the microorganisms reside in the gas side suitable arrangement may purge contaminants and waste materials from the biolayer or the biopores by occasionally seeping liquid across the membrane to the gas phase side. This purged water can leave the cell/gas interface by dripping to the bottom of the bioreactor due to gravity.

The asymmetric membrane may be formed from any material or assemblage of materials that provide a bio-layer and a hydration layer with the functionality as described. In one form the bio-layer comprise hydrophilic materials that readily supply water throughout the bio-pores and up to the surface of the bio-layer's gas contacting side. The use of hydrophilic materials for the less porous hydration layer will enhance performance of the membrane by allowing easy movement of the water through the membrane. In many instances the bio-layer and the hydration layer will comprise the same material with the hydration layer taking the form of a skin on one side of the asymmetric membrane. A hydration layer comprising a skin layer will normally also occludes the bio-pores to prevent migration of microorganisms into the liquid medium.

Utilization of the asymmetric membrane to place the active surface of the membrane in the gas phase or configuration that keep the active surface in contact with the liquid phase permits the bioreactor system to take on a variety of configurations. Either type of arrangement may comprise hollow fibers or flat sheets whether in flat or spiral wound configurations. Suitable hollow fiber membranes may place the bio-layer or the hydration layer on the lumen side. Suitable housings may retain the membrane for co-current, counter-current, or cross-flow with respect to the circulation of the liquid on one side of the membrane and the bulk gas flow on the opposite side. In the case of hollow fibers, circulation of the syngas on the outside of the fibers facilitates a horizontal orientation of the fibers so that the bioreactor may work well whether extending in a principally horizontal or vertical direction.

Circulation of liquid on the lumen side of hollow membranes provides a well defined liquid flow path and provides a contiguous space for gas flow on the outside of the membrane. This permits very high density packing of the asymmetric membrane elements without fear of disrupting liquid flow patterns and creating stagnant areas for the circulating fluid.

Many commercial organizations supply such membranes primarily in two important geometries—hollow fiber and flat sheets. These can then be made into modules by appropriate potting and fitting and these modules have very high surface area of pores in small volumes.

Suitable hydrophobic microporous hollow fiber membranes for forming a biolayer in the liquid medium are well known. An example of commercial membrane modules for such applications is the Liqui-Cel® membrane contactor from Membrana (Charlotte, N.C.), containing the polypropylene (PP) X40 or X50 hollow fibers. CELGARD® microporous PP hollow fiber membrane, containing the X30 fibers, is also available from Membrana for oxygenation applications. Liqui-Cel® membrane modules suitable for large scale industrial applications have large membrane surface areas (e.g., 220 $m^2$ active membrane surface area for Liqui-Cel® Industrial 14×28). Some characteristics of these fibers are given in the Table 1 below.

TABLE 1

| | X30 | X40 | X50 |
|---|---|---|---|
| Porosity (nominal) | 40% | 25% | 40% |
| Pore Size | 0.03 μm | 0.04 μm | 0.04 μm |
| Internal Diameter | 240 μm | 200 μm | 220 μm |
| Outer Diameter | 300 μm | 300 μm | 300 μm |
| Wall Thickness | 30 μm | 50 μm | 40 μm |

A microporous PP hollow fiber membrane product (CellGas® module) is available from Spectrum Laboratories (Rancho Dominguez, Calif.) for gentle oxygenation of bioreactors without excessive shear to the microbial or cell cultures. This PP hollow fiber is hydrophobic, with a nominal pore size of 0.05 μm and a fiber inner diameter of 0.2 mm.

For the use of hydrophobic microporous membranes for afore-mentioned applications, it is necessary to properly manage the pressure difference across the membrane to avoid formation of bubbles in the liquid. If the pressure difference is greater than a critical pressure, the value of which depends on properties of the liquid and the membrane, liquid can enter the pore ("wetting") and the gas transfer rate is significantly impeded.

To prevent wetting of pores during operations, some composite membranes have been developed by the membrane suppliers. The SuperPhobic® membrane contactor from Membrana keeps the gas phase and liquid phase independent by placing a physical barrier in the form of a gas-permeable non-porous membrane layer on the membrane surface that contacts the process liquid. The SuperPhobic® 4×28 module contains 21.7 $m^2$ membrane surface area. Another composite hollow fiber membrane with an ultra-thin nonporous membrane sandwiched between two porous membranes is available from Mitsubishi Rayon (Model MHF3504) in the form of composite hollow fibers having at 34 $m^2$ membrane area per module.

The process can use non-porous (dense) polymeric membranes that separate gases by the selective permeation across the membrane wall. The solubility in the membrane material and the rate of diffusion through the molecular free volume in the membrane wall determine its permeation rate for each gas. Gases that exhibit high solubility in the membranes and gasses that are small in molecular size permeate faster than larger, less soluble gases. Therefore, the desired gas separation is achieved by using membranes with suitable selectivity in conjunction with appropriate operating conditions. For example, Hydrogen Membranes from Medal (Newport, Del.) are used in recovery or purification of hydrogen with preferential permeation of hydrogen over $CO_2$ Medal also provides membranes for $CO_2$ removal with preferential permeation of $CO_2$.

In addition, composite membranes having a thin nonporous silicone layer on the surface of polypropylene microporous hollow fibers have been fabricated by Applied Membrane Technology, Inc. (Minnetonka, Minn.) and Senko Medical Instrument Manufacturing (Tokyo, Japan) and evaluated for artificial lung applications. See "Evaluation of Plasma Resistant Hollow Fiber Membranes for Artificial Lungs" by Heide J. Eash et al. ASAIO Journal, 50(5): 491-497 (2004).

The membranes made of poly(vinylidene fluoride) (PVDF), polyethylene (PE), PP, poly(vinyl chloride) (PVC), or other polymeric materials may also prove quite useful. The typical pore size is in the range of 0.03 to 0.4 µm. The typical hollow fiber outer diameter is 0.5 to 2.8 mm and inner diameter 0.3 to 1.2 mm.

Other useful membranes comprise hollow fiber membranes made of polymethylpentene (PMP). These PMP hollow fibers are non-porous and of either the skinned asymmetric or dense type as described in "Evaluation of Plasma Resistant Hollow Fiber Membranes for Artificial Lungs" by Heide J. Eash et al. ASAIO Journal, 50(5): 491-497 (2004) and U.S. Pat. No. 7,118,672 B2.

A hollow fiber membrane SteraporeSUN™, available from Mistubishi Rayon (Tokyo, Japan), is made of PE with modified hydrophilic membrane surface. The hollow fiber has a nominal pore size of 0.4 µm and a fiber outer diameter of 0.54 mm. A SteraporeSUN™ membrane unit Model SUN21034LAN has a total membrane surface area of 210 m$^2$, containing 70 membrane elements Model SUR334LA, each with 3 m$^2$ membrane area.

Another hollow fiber membrane SteraporeSADF™ is available from Mitsubishi Rayon. This membrane is made of PVDF with a nominal pore size of 0.4 µm and a fiber outer diameter of 2.8 mm. Each SteraporeSADF™ membrane element Model SADF2590 contains 25 m$^2$ membrane surface area, and each StreraporeSADF™ membrane unit Model SA50090APE06 containing 20 SADF2590 membrane elements has a total membrane surface area of 500 m$^2$.

Kubota Corporation (Tokyo, Japan) markets submerged membrane systems for membrane bioreactors. These membranes are of the flat-plate configuration and made of PVC with a pore size of 0.4 µm. Each membrane cartridge has 0.8 m$^2$ membrane surface area, and a Model EK-400 membrane unit, containing 400 membrane cartridges, has a total membrane area of 320 m$^2$.

Suitable membranes for where the gas contact surface retains the microorganism use asymmetric membranes having a porous layer and a less permeable layer. The porous layer, referred to as the bio-layer may comprise any material suitable for the formation of the bio-pores and the transport of liquid to and away from the microorganisms in the bio-pores. The less porous layer, referred to as the hydration layer will control the transport of the fermentation liquid to and from the bio-layer for nourishing the microorganisms and maintain effluent products at desired concentrations. The bio-layer and hydration layer are described as single layers but either may comprise several layers.

The asymmetric membrane also requires material that will provide support to the membrane structure and will occlude the internal end of the bio-pores to prevent microorganisms and other biological material from passing into the fermentation liquid. The asymmetric membrane may contain additional layers for internal support and formation of the bio-pores or the bio-layer and/or hydration layer may serve these functions as well. Any additional layers must permit direct contact of syngas with the microorganisms in the bio-pores and the permeation of liquid into the bio-layer.

The bio-layer must define the bio-pores for retaining the microorganisms in direct contact with the syngas. The biopores typically require an effective diameter of at least 1 μm over at least a portion of its length. The term effective diameter refers to the open cross-sectional area of a regularly shaped pore that would provide the same cross sectional area. The pores need not have a uniform cross section and bio-pores having an effective diameter of 1 μm over at least a third of its length will work well. The size of the bio-pores in the bio-layer of the membrane will usually have an effective diameter substantially greater than 1 μm, preferably in the range of 2 to 100 μm, and most preferably in the range of 5 to 50 μm. Typical depths of the bio-pores range from 50 to 500 μm which generally corresponds to the thickness of the bio-layer.

At minimum the hydration layer must have restricted liquid permeability with respect to the biolayer. The restricted permeability prevents excessive fermentation liquid from migrating into the bio-layer during normal operation of the system and interfering with contact between the gas and microorganisms. In most cases the hydration layer will comprise a higher density material than the bio-layer that restricts liquid flow while also occluding the internal end of the bio-pores to block migration of the microorganisms into the fermentation liquid.

Particularly suitable forms of asymmetric membranes are porous membranes with a tight (i.e., having small pores) thin "skin" on one surface of the membrane that provides the hydration layer and a relatively open support structure underneath the skin that provides the bio-layer and defines the bio-pores. The skin will typically comprise a semi-permeable layer having a thickness of from 0.5 to 10 μm. The skinned asymmetric membrane can include an "integrally skinned" membrane prepared by using phase inversion of one polymer or a composite membrane, where a thin layer of a certain material is formed on top of a porous sublayer of a same or different material. General description of asymmetric membranes and methods of their preparation can be found in the literature (e.g., Cheryn, M., Ultrafiltration and Microfiltration Handbook, Technomics Publishing Company, Lancaster, Pa., 1998; and Mulder, M., Basic Principles of Membrane Technology, $2^{nd}$ Edition, Kluwer Academic Publishers, Norwell, Mass., 1996).

A suitable skin layer has a pore size that is smaller than the size of microbial cells to prevent the cells from passing through the membrane skin but the opposite surface of the membrane has large openings that allow cells to enter and leave the bio-pores of the membrane wall. Typically, the pore size of the skin layer is less than 0.5 μm, preferably less than 0.25 μm, and most preferably in the ultrafiltration range of nominal MWCO of 10 to 300 kDa and more preferably in the range of 10 to 100 kDa.

Several asymmetric ultrafiltration membranes are available from Millipore Corporation (Bedford, Mass.), including but not limited to the Amicon Membranes and the Ultracel PLC Membranes. The Amicon Membranes are made of polyethersulfone and with a range of a nominal MWCO of 30 kDa for Amicon PM30. The Ultracel PLC Membranes, which are composite membranes made from casting the regenerated cellulose membrane onto a microporous polyethylene substrate, are available in the pore size range from 5 kDa (PLCCC) to 1000 kDa (PLCXK). Additional examples of asymmetric membranes are the MMM-Asymmetric Super-Micron Membranes and BTS Highly Asymmetric Membranes, both available from Pall Corporation (East Hills, N.Y.). The MMM-Asymmetric Membranes, available in pore size range from 0.1 to 20.0 μm, are made of polysulfone and polyvinylpyrrolidone. The BTS Highly Asymmetric Membranes, available in pore size range from 0.05 to 0.80 μm, are cast of polysulfone with a "cut off" layer of about 10 µm and a total thickness of about 120 µm.

Hollow fiber membrane modules containing asymmetric ultrafiltration membranes are commercially available from a number of membrane manufacturers. For example, the Kros-Flo® Max Module Model KM5S-800-01N from Spectrum Laboratories (Rancho Dominguez, Calif.) has 22.0 m² membrane surface area of asymmetric polysulfone hollow fiber membranes with 0.5 mm fiber inner diameter, a tight skin on the lumen side, and a pore rating of 50 kDa. ROMICON® polysulfone hollow fiber membranes available from Koch Membrane Systems (Wilmington, Mass.) are also asymmetric with the tight skin on the lumen side. ROMICON cartridge Model HF-97-43-PM50 is a 6-inch module containing fibers of 1.1 mm inner diameter and 50 kDa nominal MWC at 9.0 m² total membrane surface area.

Thus bio-support membrane used in the instant invention can be microporous, non-porous, or composite membranes or any combination thereof. Any suitable potting technique can be used to collect and provide the necessary assembly of individual membrane elements. If microporous, hydrophobic membranes are preferred due to faster diffusion of gases in the gas-filled pores than liquid-filled pores.

The feed gas flows through the gas side of the membrane module continuously or intermittently. The feed gas pressure is in the range of 0.1 to 100 bars, preferably 0.3 to 30 bars, and most preferably 0.7 to 15 bars. Operating at higher gas pressures has the advantage of increasing the solubilities of gases in the liquid and potentially increasing the rates of gas transfer and bioconversion. The differential pressure between the liquid and gas phases is managed in a manner that the membrane integrity is not compromised (e.g., the burst strength of the membrane is not exceeded) and the desired gas-liquid interface phase is maintained.

In such membranes the gas and liquid can be brought into direct and intimate contact without creating any bubbles by operating at a differential pressure that is below the bubble point of the membrane liquid interface and maintains the gas-liquid interface. Furthermore, the properties of this interface can be controlled by the porosity and hydrophobicity/hydrophilicity properties of the membrane pores.

Where the microorganisms reside in the gas side, the gas side pressure is normally slightly higher than the liquid pressure to prevent convective liquid flow from the hydration layer (liquid) side to the open surface (gas) of the gas contacting side. The higher pressure can also reduce the formation of any liquid layer at the cell/gas interface, which would impede gas transfer to the cells.

The particular application and type of membrane used therein will dictate the desired flow rate through the groups of modules. In the case of gas flow through the lumen of a hollow fiber membrane, acceptable gas flow velocities will typically range from 1 to 50 cm/s. In the case of gas flow on the outside of membrane, i.e. the shell side of the module, the bulk gas velocity varies from 0.1 to 10 cm/s when calculated on the basis of the gas volume across net cross sectional area of the module minus the fiber volume.

The gas velocity through the membrane along with the relative humidity of the gas present the two primary factors controlling the existence of liquid plugging in the gas channels of membrane. In the case of passing a syngas through the lumen of a hollow fiber membrane, water vapor saturates the gas within the first a few inches of the membrane due to water vapor diffusion from liquid side under the conditions typical in syngas fermentation. Once saturated, water starts to condense immediately in the syngas because of its decrease in volume as it feeds the microorganisms retained by the membrane thereby producing more liquid in the form of products. This condensation persists until the syngas exits from the fiber.

If the gas velocity decreases to a low enough value the condensate formed in a fiber can block the fiber lumen in which it flows. The lumen blocking will not only decrease the gas transfer (or gas consumption) by reducing effective membrane area, but also increase gas pressure drop by reducing the channel area for gas flow. Once blocking occurs, temporary increases in pressure drop through the fiber may reestablish gas flow.

Looking specifically at the problem in hollow fibers water vapor permeation in hollow fibers can be described according to Eq. 1, where the rate of relative humidity (RH) changes along the fiber in proportional to the water vapor transfer coefficient (K) and the difference between full gas saturation (RH=1) and the actual saturation RH. In the equation, x is a distance from the fiber inlet (m), $Q_{gas}$ is gas flow rate (m³/s), d is internal fiber diameter (m), and n is the number of fiber (–).

$$\frac{dRH}{dx} = \frac{\pi dnK}{Q_{gas}}(1 - RH) \quad (1)$$

Using boundary conditions: $RH=RH_0$ at x=0 and $RH=RH_L$ at x=L (Eq. 2) can provide the value of K.

$$K = \frac{Q_{gas}}{\pi dnL} \text{Ln} \frac{1 - RH_0}{1 - RH_L} \quad (2)$$

Example 1

To analyze a specific membrane operation and geometry, a module with 275 0.2 meter-long microporous polyethylene hollow fiber membranes was used to estimate water vapor transfer coefficient, K. Fiber inner diameter and pore size was 410 µm and 0.4 µm, respectively. Relative humidity in the inlet and outlet gas was measured with a psychrometer (RH92 model, Omega Engineering Inc.) at an ambient temperature of 37° C. When gas flow rate was 1 L/min (or 0.46 m/s in fiber lumen), relative humidities in inlet and outlet were measured at 0.05 and 0.945, respectively. Finally, water vapor transfer coefficient, K, was calculated at $6.7 \times 10^{-4}$ M/s using Eq. 2.

This K value again can be put in Eq. 2 to calculate the distance (L) required to saturate gas traveling through lumen. Under the identical condition used in the above experiment, the relative humidity of the gas increases to 99% before it travels 0.06 m. As mentioned earlier, water vapor starts to condense as soon as it saturates and this condensation persists in the rest of the fiber length.

Example 2

The experiment of Example 1 was repeated with a commercial module, Liqui-Cell® 2.5×8 (Membrana GmbH, Germany) under identical condition. The membrane fibers in the module were micro-porous like the membrane used in the above Example 1. The inner diameter of the membrane fiber was 220 micron. The diameter and length of the module were 63.5 mm and 203 mm, respectively. A very high water vapor transfer rate kept the relative humidity in the exit gas always above 99% even at the maximum gas flow rate allowed by the experimental setup, i.e. 7 L/min. Since the water vapor transfer coefficient, K, was not obtainable under this condition, the minimum water vapor transfer rate ($K_{min}$) was calculated for the condition. When gas velocity in membrane lumen is 0.1 m/s, the relative humidity of the gas reaches 99% before it travels 0.03 m based on the $K_{min}$, i.e. $7.7 \times 10^{-4}$ m/s.

Example 3

One more experiment was run with a non-porous membrane, SuperPhobic® 2.5×8 (Membrana GmbH, Germany), which did not have a micro-porous layer. Instead it had a non-porous layer that prohibited direct water vapor evaporation through membrane. As a result, water vapor transfers were inherently lower than those of porous membranes. The dimensions of this module were identical with the Liqui-Cell® module used in Example 2. With a gas flow of 0.83 L/min, relative humidities of inlet and outlet gas were measured at 0.05 and 0.794, respectively. Consequently, water vapor transfer coefficient, K, was calculated at $2.08 \times 10^{-5}$ m/s using Eq. 2. The required membrane length to get a relative humidity of 99% in the outlet when gas travels at 0.10 m/s was calculated at 1.11 m. Due to a gas volume contraction in membrane lumen in real fermentation conditions, the required membrane length to saturate the syngas would be a bit shorter than 1.11 m.

In syngas fermentation with a biofilm attached on hollow fiber membrane, the overall length of fibers including all membranes serially connected is more than 1.5 meter. Therefore, it is inevitable to have some degree of water condensation inside the membrane fiber regardless of the fiber characteristics.

As mentioned earlier, water vapor starts to condense as soon as it saturates and the condensation persists in the rest of the fiber. Once condensate blocks the fiber, the biofilm attached thereto receives no syngas thereby reducing the effective membrane area of the module. The excess syngas passes to other fibers at higher velocity and smaller contact time. Consequently the gas conversion efficiency and productivity of the membrane module decreases.

Example 4

To demonstrate the occurrence of condensate plugging and the influence of the gas flow rate a hollow fiber membrane was used in an experiment that delivered feed gas to a biofilm in a hollow fiber membrane. The feed gas comprised, on a volumetric basis, approximately 30% CO, 32% $CO_2$, 32% $H_2$, 3% $N_2$, and $CH_4$. The hollow fiber membrane used in this experiment had a thin non-porous layer sandwiched by two microporous hydrophobic layers in both sides (Mitsubishi Rayon Co., Japan). The inner and outer diameters of the membrane were 280 micron and 200 micron, respectively. The effective length of membrane was 0.95 m while total membrane area was estimated at 17.1 $m^2$.

For the first two weeks, the gas consumption rate increased gradually as a result of biofilm growth and afterward started to decline slowly from its peak. Over this time, the gas pressure drop between module inlet and outlet increased from well below 0.03 bars to 0.034 to 0.048 bars, which indicated a portion of the fibers were blocked and obstructing gas flow. To remove condensate out from the membrane lumen and control the lumen plugging at a low level, the gas flow rate was increased from 1 L/min to 3 L/min. As a result, gas consumption increased approximately 50% from 4.9 to 7.4 mmol/min.

Example 4 confirms that increasing the flow rate can restore gas flow to plugged fibers in the membrane. If the procedure is practiced periodically, the condensate induced fiber plugging can be controlled at low level in a long-term operation.

As one of its objects this invention seeks to avoid such liquid plugging on the gas side of the membrane. To this end the number of modules encountered by a serial flow of gas in the process of this invention will continue to decrease in number along the gas flow path to maintain enough pressure drop to avoid liquid plugging in any narrow channels. This pressure drop varies with the particular geometry of the gas flow passages as well as the gas composition. The pressure drop required to avoid liquid plugging is approximately inversely proportional to the lumen diameter. For example as opposed to the 200 μm of the fibers in Example 4, when flowing syngas through hollow fiber lumens of 500 μm diameter, pressure drop through the lumen will usually equal at least 0.01 bars and more preferably 0.02 bars to avoid plugging.

This invention is further described in the context of a bioconversion process for the production of ethanol from CO and/or mixtures of $H_2/CO_2$ using modules containing hollow fiber membranes. The description of the invention in a particular context does not restrict its application or claim coverage from other process applications that meet the criteria for its use.

This invention finds ready application to the production of acetic acid, ethanol and other products from suitable feed gas streams. Such conversions using microorganisms are well known. For example, in a recent book concise description of biochemical pathways and energetics of such bioconversions have been summarized by Das, A. and L. G. Ljungdahl, *Electron Transport System in Acetogens* and by Drake, H. L. and K. Kusel, *Diverse Physiologic Potential of Acetogens*, appearing respectively as Chapters 14 and 13 of Biochemistry and Physiology of Anaerobic Bacteria, L. G. Ljungdahl eds., Springer (2003). Any suitable microorganisms that have the ability to convert the syngas components: CO, $H_2$, $CO_2$ individually or in combination with each other or with other components that are typically present in syngas may be utilized. Suitable microorganisms and/or growth conditions may include those disclosed in U.S. patent application Ser. No. 11/441,392, filed May 25, 2006, entitled "Indirect Or Direct Fermentation of Biomass to Fuel Alcohol," which discloses a biologically pure culture of the microorganism *Clostridium carboxidivorans* having all of the identifying characteristics of ATCC no. BAA-624; and U.S. patent application Ser. No. 11/514,385 filed Aug. 31, 2006 entitled "Isolation and Characterization of Novel Clostridial Species," which discloses a biologically pure culture of the microorganism *Clostridium ragsdalei* having all of the identifying characteristics of ATCC No. BAA-622; both of which are incorporated herein by reference in their entirety. *Clostridium carboxidivorans* may be used, for example, to ferment syngas to ethanol, n-butanol and/or hexanol. *Clostridium ragsdalei* may be used, for example, to ferment syngas to ethanol.

Suitable microorganisms and growth conditions include the anaerobic bacteria *Butyribacterium methylotrophicum*, having the identifying characteristics of ATCC 33266 which can be adapted to CO and used and this will enable the production of n-butanol as well as butyric acid as taught in the references: "Evidence for Production of n-Butanol from Carbon Monoxide by *Butyribacterium methylotrophicum*," Journal of Fermentation and Bioengineering, vol. 72, 1991, p. 58-60; "Production of butanol and ethanol from synthesis gas via fermentation," FUEL, vol. 70, May 1991, p. 615-619. Other suitable microorganisms include *Clostridium Ljungdahli*, with strains having the identifying characteristics of ATCC 49587 (U.S. Pat. No. 5,173,429) and ATCC 55988 and 55989 (U.S. Pat. No. 6,136,577) and this will enable the production of ethanol as well as acetic acid. All of these references are incorporated herein in their entirety.

The microorganisms found suitable thus far for this invention require anaerobic growth conditions. Therefore the system will employ suitable control and sealing methods to limit the introduction of oxygen into the system. Since the organisms reside principally in contact with the liquid volume of the retention chamber the system maintains a suitable redox potential in the liquid and this chamber may be monitored to make insure anaerobic conditions. Anaerobic conditions in the retained liquid volume are usually defined as having a redox potential of less than −200 mV and preferably a redox potential in the range of from −300 to −500 mV. To further minimize exposure of the microorganisms to oxygen the feed gas will preferably have an oxygen concentration of less than 1000 ppm, more preferably less than 100 ppm, and even more preferably less than 10 ppm.

In one suitable form of this invention, a bio-support membrane suitable for permeation of at least one of CO or a mixture of $H_2$ and $CO_2$ provides the separation between a feed gas and a liquid phase. FIG. 1 shows more detail of the membrane configuration and interface in the operation of a representative bio-reactor system. FIG. 1(a) depicts syngas stream A flowing to the gas feed side of the membrane in gas phase maintained in a chamber on the gas contact side of the membrane. The syngas components freely diffuse through the membrane pores to the liquid interface but without formation of bubbles. The anaerobic acetogenic bacteria, *Clostridium ragsdaeli*, having all of the identifying characteristics of ATCC No. BAA-622, is maintained in a fermentation media. The fermentation media is circulated through a chamber on the opposite side of the membrane that maintains a liquid volume in contact with the liquid side of the membrane. Suitable microbial cells are present as bio-film on the liquid-contacting side of the membrane surface; converting at least one of CO or $H_2/CO_2$ in the feed gas to desirable products. Since the membrane pores are much smaller than the width of the microorganisms they preferentially stay on the membrane surface to convert CO and $H_2/CO_2$ to gain metabolic energy, grow and form a biofilm on the membrane surface. A stream B withdraws the liquid phase components from a liquid volume retained about the outer surface of the biofilm.

FIGS. 1(b)-(c) show various forms of the membrane with a biofilm present on the liquid contacting side of the membrane. The membrane portions of FIGS. 1(a) and 1(b) both schematically show a cross-section of porous membrane to the left with a biofilm layer developed on the opposite side of the membrane. The interface between the biofilm and the membrane functions as equilibrium partitioning to keep the liquid and gas phases separated from each other. FIG. 1(c) depicts a similar arrangement however this time with a nonporous membrane to the left and a biofilm adhering to the surface on the right-hand side of the membrane. FIG. 1(d) illustrates a composite structure for the membrane that positions a non-porous membrane surface in contact with the gas phase components. The opposite face (right side) of the non-porous membrane is affixed to a porous membrane and a biofilm layer adheres to the surface on the right side of the porous membrane layer.

Figure 2:
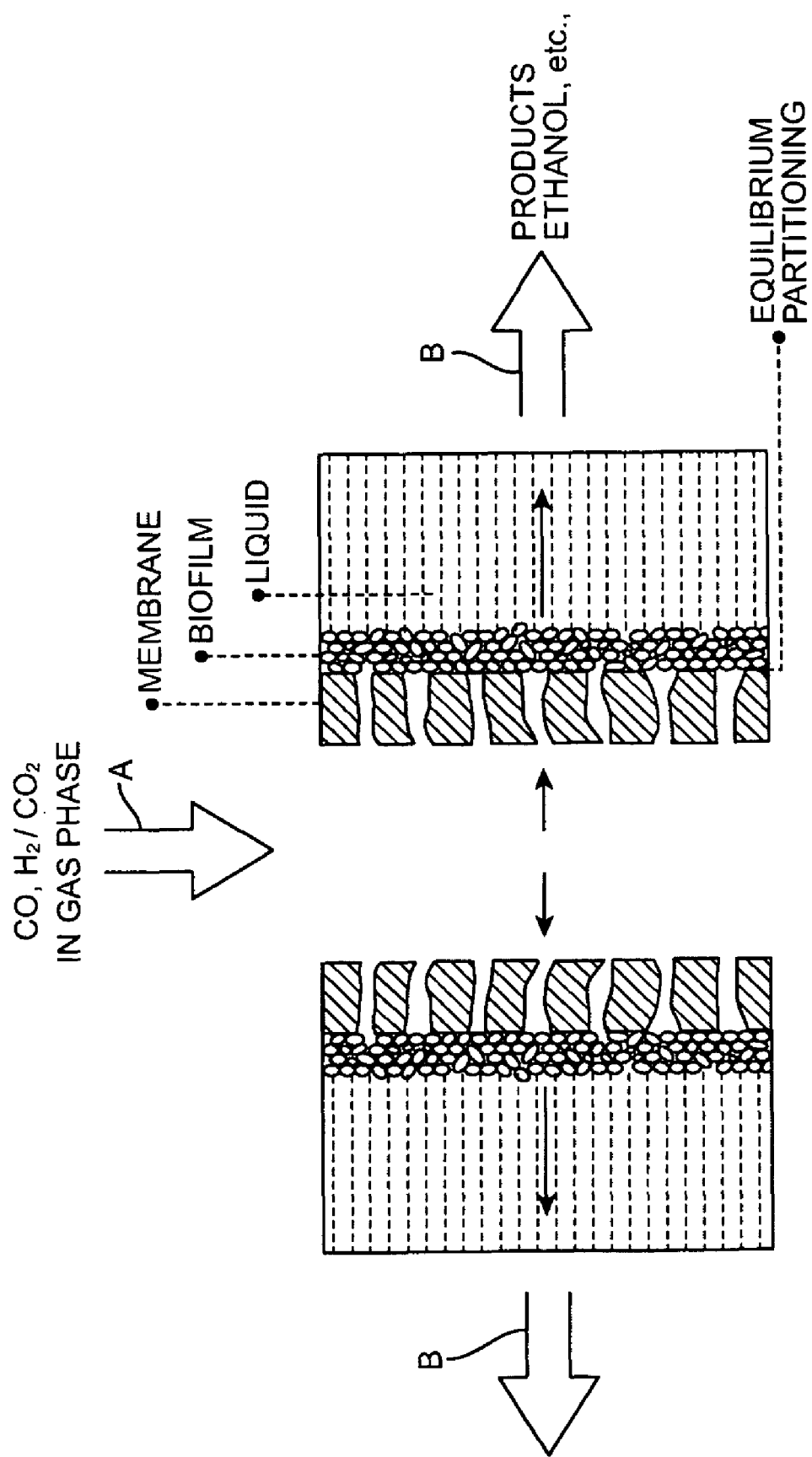
FIG. 2 is a schematic drawing showing a central passage delivering gas to two parallel membrane walls with a liquid phase to the outside of each wall.

FIG. 2 depicts a generalized view of a typical flow arrangement for efficient use of space in a membrane system. Syngas components enter the system as gas stream A and flow into a central space between two membrane walls. Gas phase contact surfaces of the opposing membrane walls form a distribution chamber for receiving gas from stream A. Gas permeates simultaneous through, in this case, the porous membrane for consumption by the microbes in the biofilm layers that adhere to the outer walls of the two opposing membranes. In this manner each gas channel serves multiple membrane surfaces and the stream B of liquid products is delivered from multiple membrane walls. The arrangement of FIG. 2 can use a flat sheet configuration and be particularly useful for good flow control and distribution on the liquid side that may be necessary for biofilm thickness control.

Figure 3:
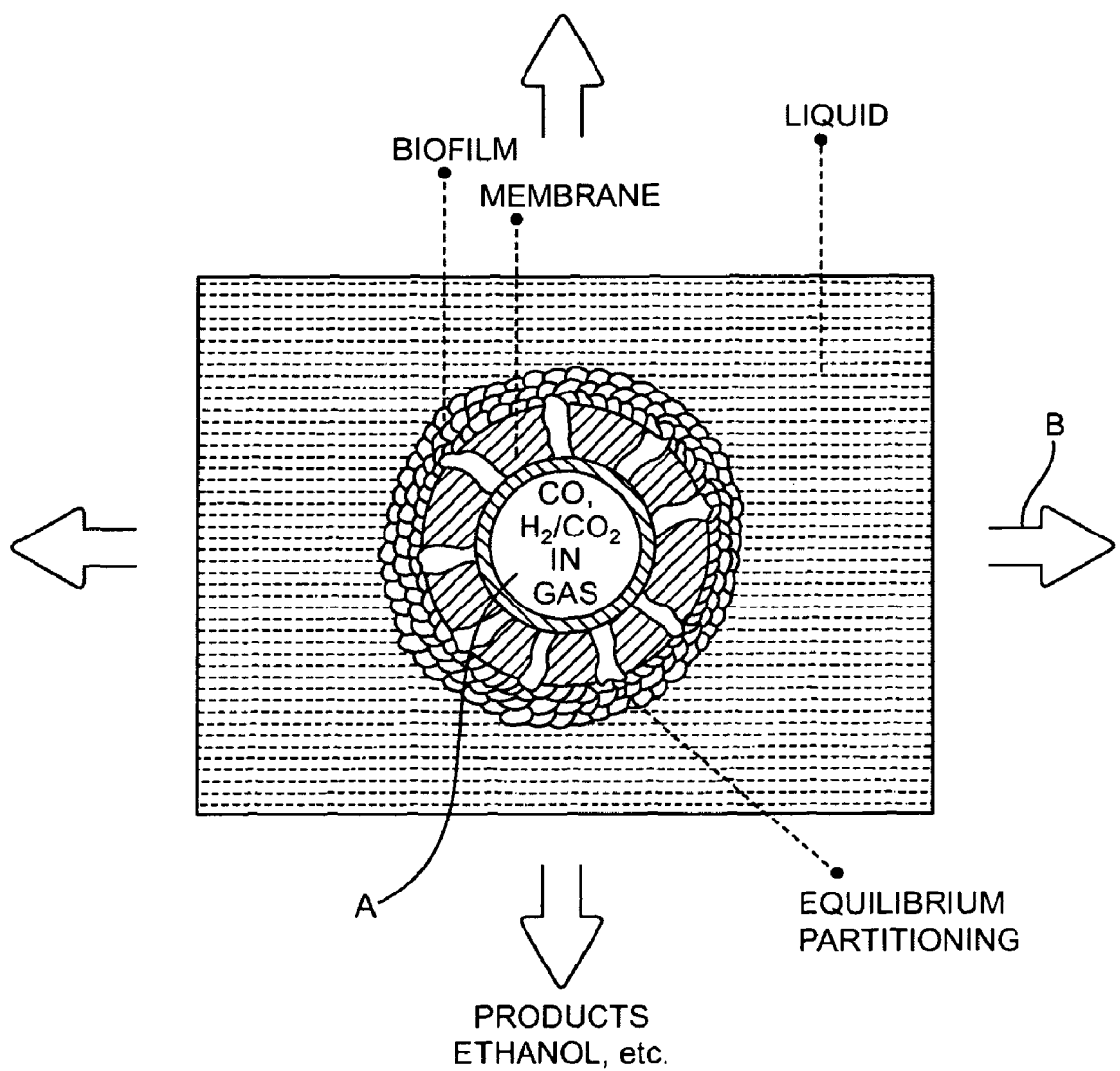
FIG. 3 is a schematic drawing showing the interior passage of FIG. 2 enclosed by the interior surface of the membrane in tubular form with liquid retained to around the membrane circumference.

FIG. 3 shows the special case of FIG. 2 wherein the opposite walls of the central distribution chamber wrap around in continuous form to provide a tubular membrane. In this case gas stream A enters the lumen of the membrane and streams B of liquid products flow away from the outer walls in all directions. Hollow fibers are particularly useful for such bioreactor configuration.

Figure 4:
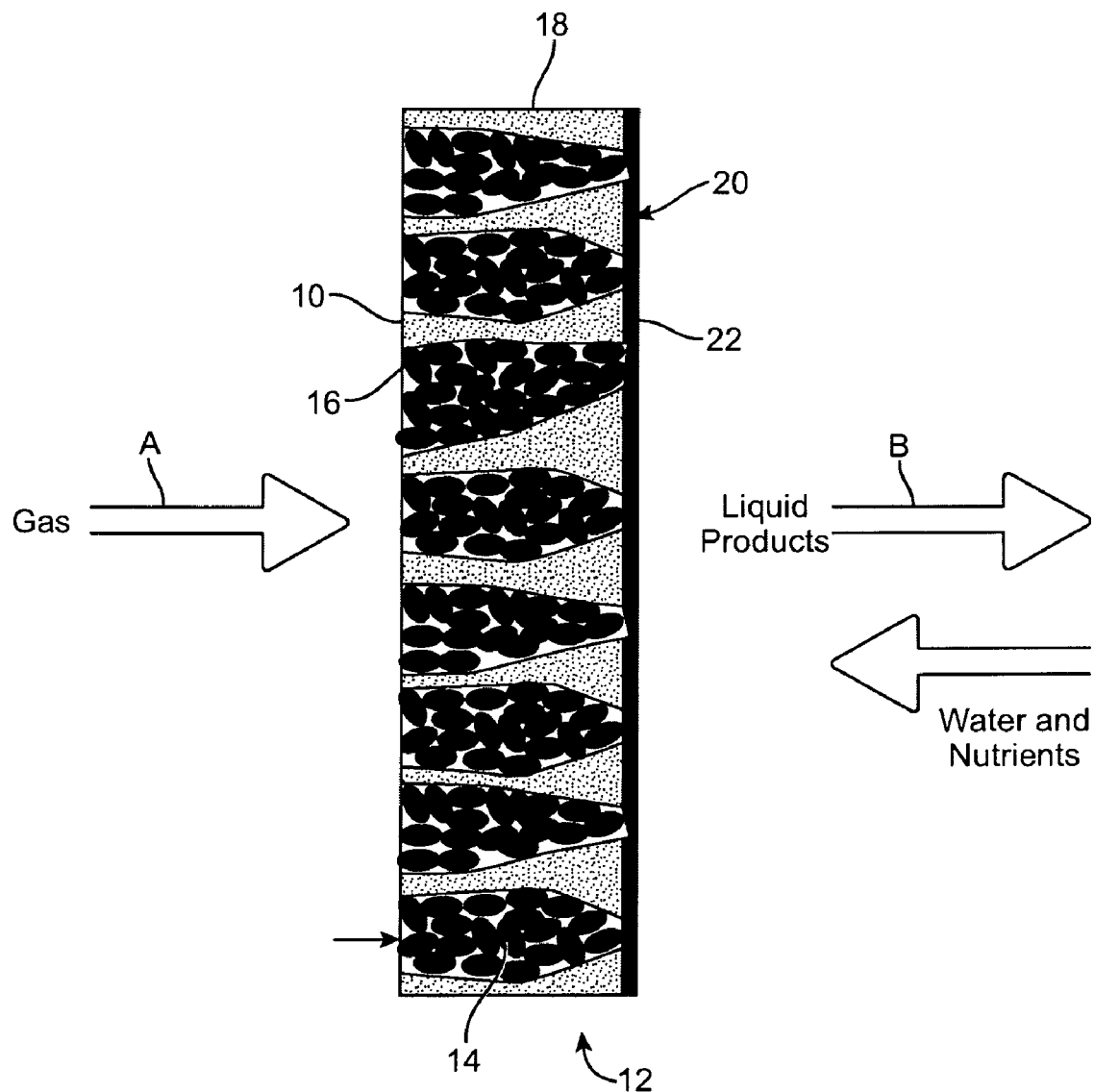
FIG. 4 is a schematic drawing showing a cross section of an asymmetric membrane with gas stream in contact with a bio-layer that retains microorganisms therein and a hydration layer in the form of a skin in contact with liquid.

In another highly useful form of this invention, an asymmetric membrane, suitable for permeation of the fermentation liquid provides the separation between the liquid phase and feed gas comprising at least one of CO or a mixture of $H_2$ and $CO_2$ and a liquid phase. FIG. 4 shows more detail of the membrane configuration and interface in the operation of a representative bio-reactor system. FIG. 4 depicts a cross section of a single membrane element with a syngas stream A flowing to the gas contacting side 10 of the asymmetric membrane 12. The syngas components directly contact the microorganisms 14 contained in bio-pores 16. The anaerobic acetogenic bacteria, *Clostridium ragsdaeli*, having all of the identifying characteristics of ATCC No. BAA-622, is maintained in the biopores and supplied with the fermentation liquid by permeation through the bio-layer 18. The fermentation liquid circulates on the opposite side of the syngas A and permeates through a hydration layer formed as skin 20 on the inner surface of bio-layer 18. Direct contact of skin 20 with bio-layer 18 transfers the fermentation liquid to the bio-pores 16. The surfaces of bio-layer 18 that contact the microorganisms and gas stream serve as equilibrium partitioning across the asymmetric membrane to keep the liquid and gas phases separated from each other. The pores in skin 20 are much smaller than the width of the microorganisms retained in bio-pores 16 so that skin 20 occludes the inner end of bio-pores 16 and prevents the microorganisms from passing through skin 20 and to liquid contacting surface 22. As a result the microorganisms 14 preferentially stay within bio-pores 16 to gain metabolic energy by converting CO and $H_2/CO_2$ thereby growing and sustaining themselves within the bio-pores 16. A portion of liquid B is withdrawn and separated to recover the desired products from the fermentation liquid.

To load the asymmetric membrane with microorganisms, the bio-layer first is inoculated with microorganisms followed by further cell growth to reach the desired cell loading density. To inoculate the bio-layer, an aqueous solution containing microorganisms is introduced to the gas contacting side of the asymmetric membrane, and then the solution is slowly filtered through the bio-layer and hydration layer by applying a slight trans-membrane pressure, creating a microorganism-free filtrate through the hydration layer and entrapping cells within the bio-pores of the bio-layer. The microorganism-containing membrane is incubated for further microorganism growth, by contacting the membrane with a liquid solution containing nutrients and carbon source suitable for microorganism growth. Alternatively, the membrane can be incubated using a syngas and a liquid solution containing nutrients.

Figure 5:
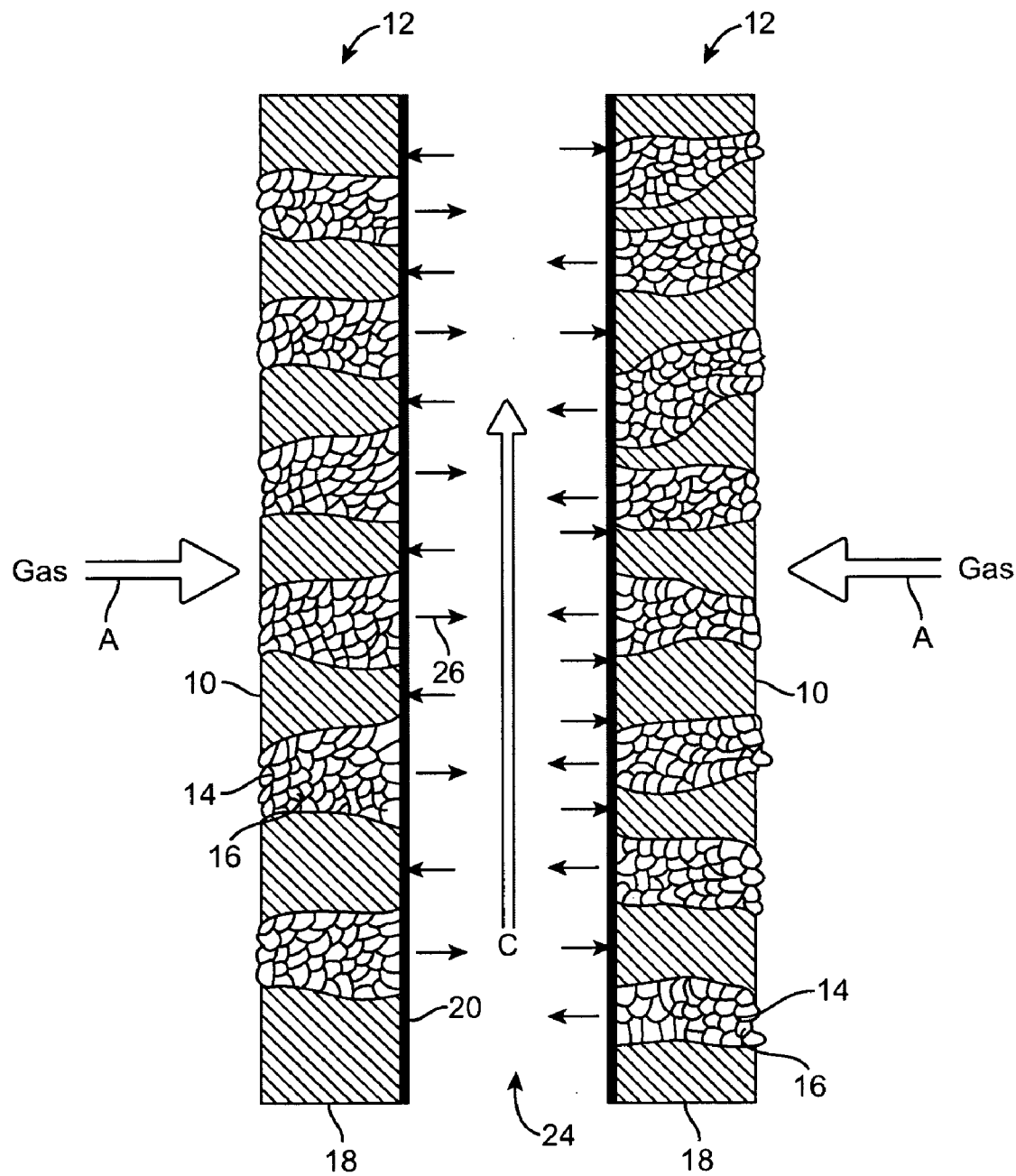
FIG. 5 is a schematic drawing showing a central passage formed by two membranes of the type shown in FIG. 4 with a gas stream contacting the outer wall and liquid contacting the inner walls.
Figure 6:
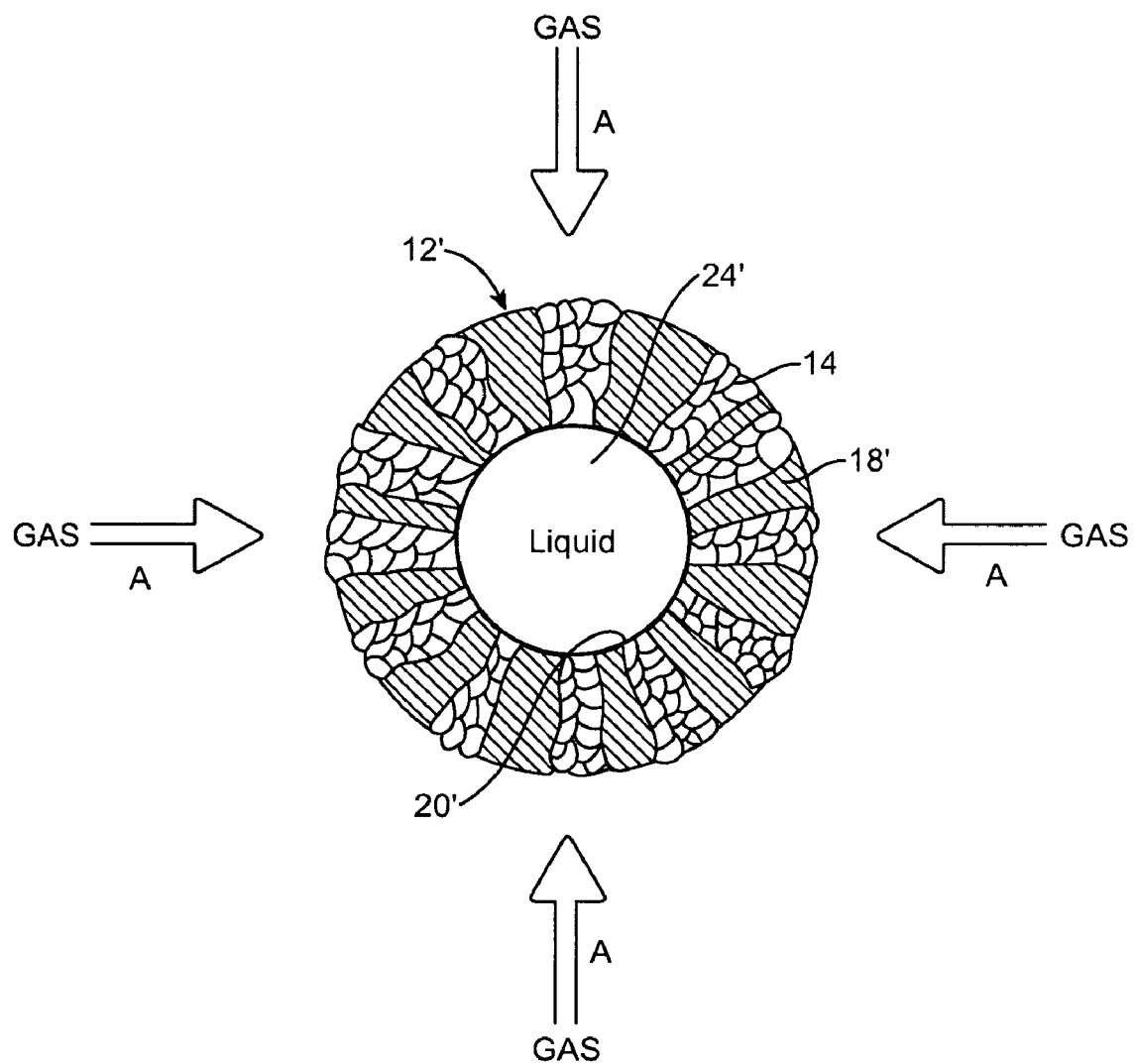
FIG. 6 is a schematic drawing showing a transverse cross-section of the asymmetric membrane of FIG. 4 made into a hollow fiber with the bio-layer on the outside and the hydration layer on the inside.

FIGS. 5 and 6 show various configurations of asymmetric membranes with microorganisms present within bio-pores of the bio-layers. In FIG. 5 two asymmetric membrane portions 12 border a central liquid channel 24 through which a fermentation liquid circulates in the direction of stream C. The asymmetric membranes on each side of liquid channel 24 functions in a similar manner to that described for the single membrane element of FIG. 4. Syngas flows across gas contacting side 10 into contact with microorganisms 14 and fermentation products passing out skin 20 in the direction of arrows 26. The arrangement of FIG. 5 can use a flat sheet configuration or a tubular configuration and be particularly useful for good flow control and distribution on the liquid side FIG. 6 shows a special case of FIG. 5 wherein the asymmetric membrane 12' wraps around in continuous form to provide a tubular membrane with a central liquid channel 24'. In this case the syngas stream A flows radially inward into contact with the microorganisms 14 contained within an annular bio-layer 18'. The skin 20' covers the inner surface of biolayer 18' and controls the permeation of liquid across biolayer 18'.

An alternate configuration for a tubular configuration of an asymmetric membrane (not shown) can reverse the skin and bio-layer locations from that of FIG. 6. In such a case the liquid contacts the outer surface of the asymmetric membrane 12" and liquid permeates to bio-layer located inside membrane 12". The central passage 24" now serves to supply the syngas to the inner surface of the membrane.

Figure 8:
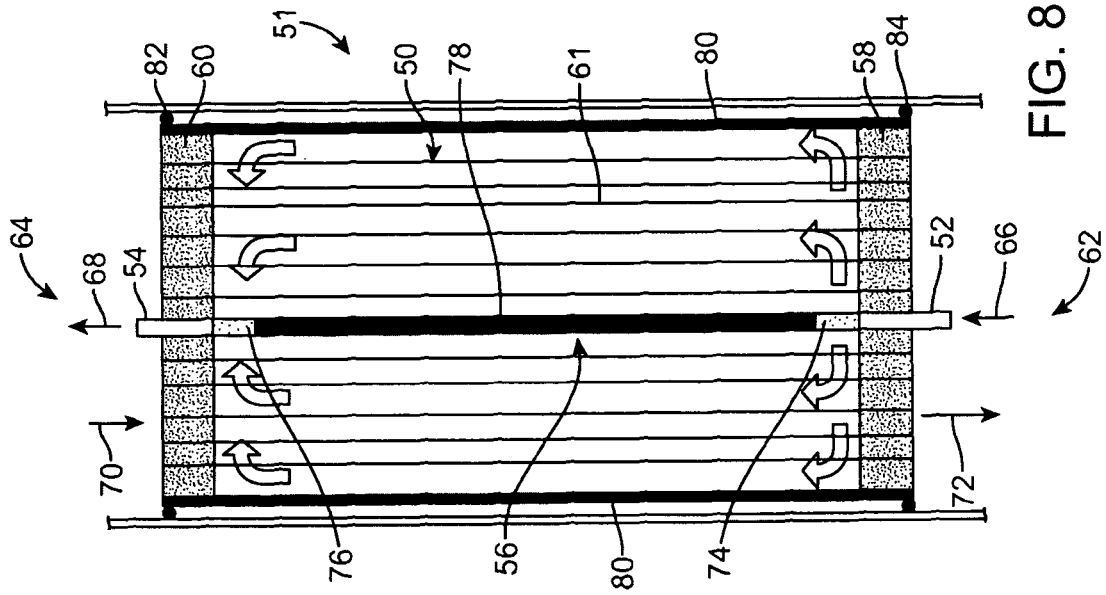
FIG. 8 is a schematic drawing of two-headed membrane modules for use in a bioreactor system with means for inter fiber circulation of gas or liquid.
Figure 7:
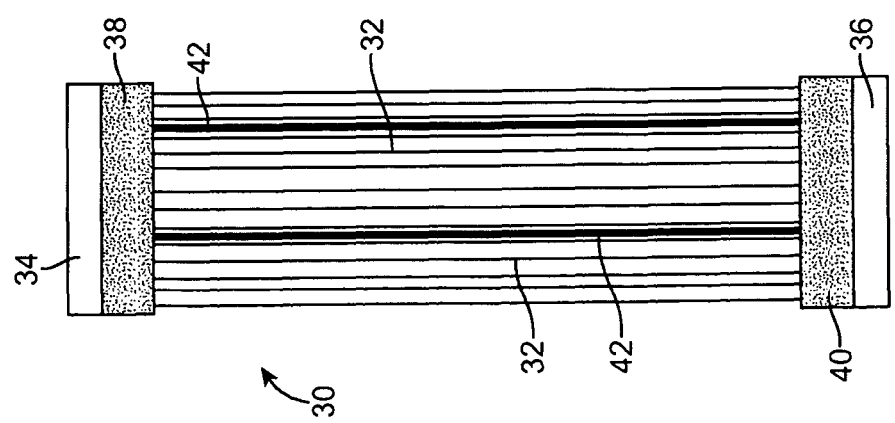
FIG. 7 is a schematic drawing of a two-headed membrane module, respectively, for use in a bioreactor system with gas and liquid circulation.

The membranes can be configured into typical modules as shown in FIGS. 7 and 8 for hollow fibers. The fibers provide gas-permeable membrane surfaces in the form of microporous and/or nonporous hollow fibers. The gas or liquid flows in the fine fibers that are bundled and potted inside a cylindrical shell or vessel through which the liquid is distributed and circulated. Very high surface areas in the range of $1000 \, m^2$ to $5000 \, m^2$ per $m^3$ can be achieved in such modules.

FIGS. 7 and 8 schematically show fibers potted in two-headed membrane module configurations for use in a bioreactor system with gas and liquid circulation. A hollow fiber wall of each hollow fiber defines a hollow fiber lumen and an outer surface. The vertical orientation of the fibers maintains them in the desired position and avoids displacement due to gravity and/or buoyancy forces. The membranes forming the hollow fibers can be gas-permeable microporous and/or nonporous membranes.

In alternate arrangement process gas may fill the hollow fiber lumens and the process liquid contacts the outside of hollow fibers or the process liquid may fill the fiber lumens and the process gas contacts the outside of the hollow fibers. In either of these arrangements the lumen side or the outside the membrane surface may retain the microorganisms in either a biofilm immersed in the liquid or in the gas side preferably as a biolayer occupying biopores. Where membrane of the module retains the biofilm in the liquid phase, process gas passes through the hollow fiber wall to interact with the biofilm to generate a liquid product that mixes with the process liquid. If the membrane module retains the microorganisms in the gas side, liquid permeates through the membrane to bring liquid and nutrients to the microorganisms to consume the process gas and generate liquid products that permeate back through the membrane into the liquid phase.

In either case the process gas can be a synthesis gas (syngas), such as a mix of CO, $H_2$ and $CO_2$ with other components such as $CH_4$, $N_2$, $NH_3$, $H_2S$ and other trace gases, or the like. With such a gas the biofilm or biolayer will likely support a culture, such as *Clostridium ragsdalei, Butyribacterium methylotrophicum, Clostridium ljungdahlii, Clostridium carboxidivorans*, combinations thereof, and the like, which can generate the liquid product from the syngas. Such liquid product typically comprise(s) ethanol, n-butanol, hexanol, acetic acid, butyric acid, combinations thereof, and the like, depending on the syngas and culture selected. Those skilled in the art will appreciate that numerous combinations of syngas and culture can be selected as desired for generating a particular liquid product desired.

FIG. 7 illustrates a two-headed membrane module arranged for inward fluid flow from the outer circumference of the module for contact of the outer fiber surface. This membrane module 30 includes a number of hollow fibers 32, each having a hollow fiber wall defining a hollow fiber lumen and an outer surface. A fluid chamber 34 operably connected one end of the hollow fibers 32 to communicate fluid with one end of the hollow fiber lumens and fluid chamber 36 operably connects the other end of the hollow fibers 32 to permit circulation of fluid through the hollow fiber lumens. An epoxy or other like substance provides a potting material that secures hollow fibers 32 in heads 38 and 40 for communication of the lumens of fibers 32 through chambers 34 and exhaust 36, respectively. A number of support rods 42 secure heads 38 and 40 in spaced apart relationship to provide mechanical strength to the membrane module 30, which must withstand forces caused by buoyancy of the hollow fibers, weight of the hollow fibers and biofilm, membrane module handling, and the like. The length of the hollow fibers 32 can be greater than the distance between the gas inlet head 38 and 40 to give the hollow fibers 32 some slack and freedom to move. In one embodiment, the hollow fibers have a length equal to 1.015 to 1.15 times the distance between the potted ends of head 38 and 40 to produce slack in the fibers and preferably a length equal to 1.015 to 1.03 times the distance between heads 38 and 40.

FIG. 8 depicts a membrane module 50 housed within a vessel wall 51 and arranged for countercurrent flow through the membrane modules: the process fluid in contact with the outside of the lumens enters the bottom of the membrane module and exits the top, and the process fluid passing through the lumens enters the top of the membrane module and exits the bottom. Those skilled in the art will appreciate that the membrane modules can be countercurrent flow or concurrent flow, with the process liquid or process gas entering the top or the bottom of the membrane module, as desired for a particular application.

As illustrated in FIG. 8, bottom fluid connection 52 and top fluid connection 54 are connected to or part of the tube 56 where the tube 56 passes through the bottom potted end 58 and the top potted end 60, respectively. The fluid connections 52 and 54 can attach to piping that passes out of the membrane vessel or attach to fluid connections of adjacent membrane modules when a number of membrane modules are connected in series within a membrane vessel. The hollow fibers 61 pass through the potted ends 58, 60, so that the hollow fiber lumens are open to bottom space 62 and top space 64. The bottom space 62 and top space 64 can communicate with piping that passes out of the membrane vessel or adjacent membrane modules when a number of membrane modules are connected in series within a membrane vessel. In this arrangement, process liquid or gas stream 66 enters the membrane module 50 at the bottom fluid connection 52 and exits through the top liquid connection 54 as stream 68. The other of the process gas or the process liquid enters the membrane module 50 at the top potted end 60 as stream 70 and exits the bottom potted end 58 as stream 72. A seal ring 82 positioned at the top of the module between head 60 and vessel wall 51 in conjunction with a seal ring 84 at the bottom of the module between head 58 and vessel wall 51 blocks communication of the fluid that contacts the outer surface of fibers 61 and the fluid present in bottom space 62 and top space 64.

Tube 56 runs the length of the membrane module between the bottom potted end 58 and the top potted end 60. Tube 56 includes a bottom perforated section 74 near the bottom potted end 58, a top perforated section 76 near the top potted end 60, and a blocked section 78 between perforated section 72 and 74. In this arrangement as indicated by the hollow arrows, process fluid in the tube 56 passes out the bottom perforated section 74, along the outer surfaces of the hollow fibers 61, into the top perforated section 76. Blocking by the middle section 78 forces process fluid to flow radially into contact with the outer surfaces of the hollow fibers 61. The tube primarily functions to distribute and collect liquid from the fibers 56 about central area of the potted ends 58 and 60 and can also serve as a central support between the potted ends. If central support is not needed, the continuous tube may be replaced with simple distributors and collectors, and a number of support rods 80 secure heads 58 and 60 in spaced apart relationship.

Figure 9:
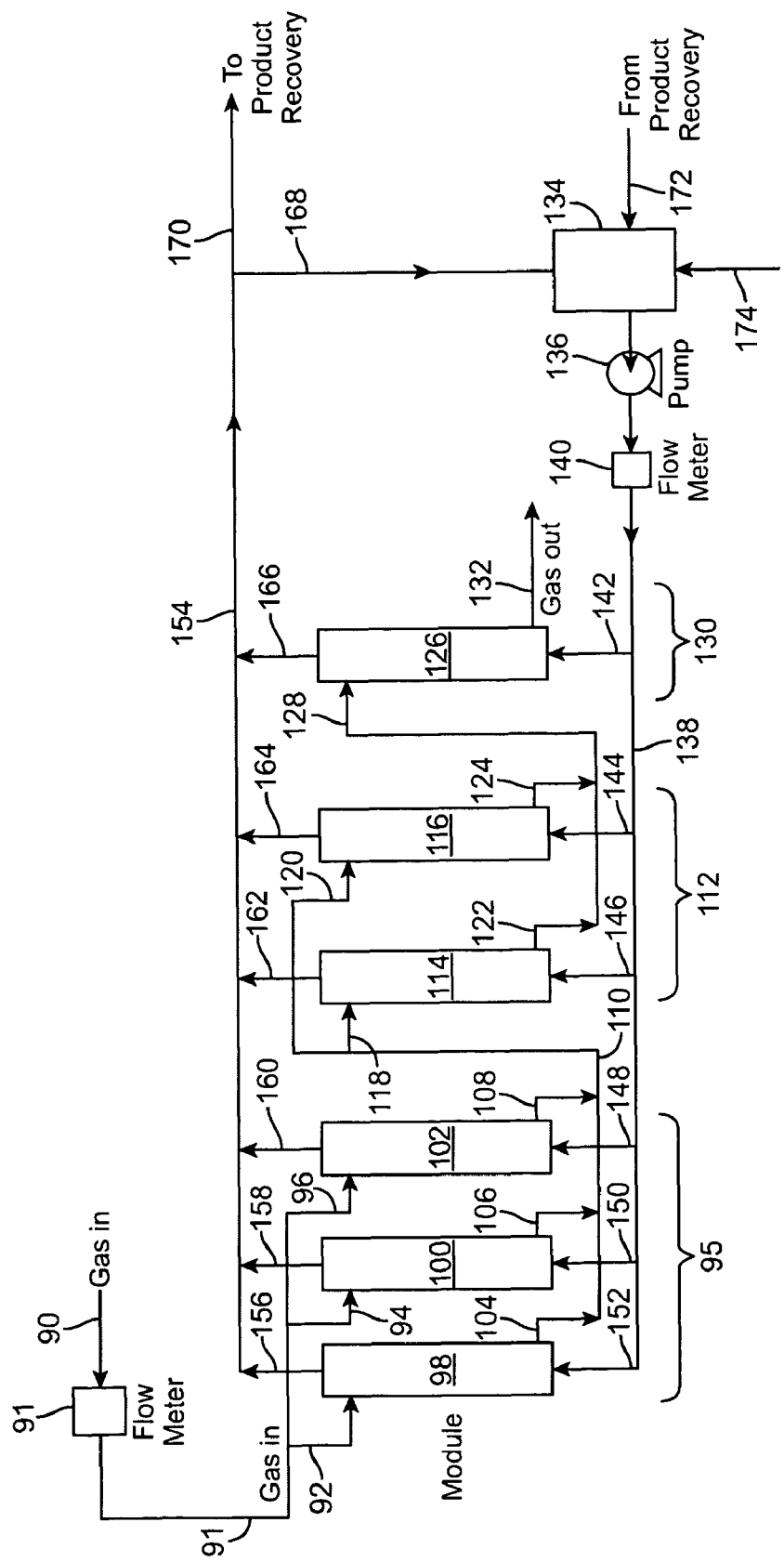
FIG. 9 is a schematic drawing showing a bioreactor system circulation of gas and liquid to groups of modules.

One form of the invention may apply to single modules or single stacks of modules surrounded by their own vessel. FIG. 9 schematically depicts such a process arrangement. A feed gas stream flows to the process via line 90 at a volumetric rate measured by flow meter 91. Lines 92, 94, and 96 distribute the gas to a group of modules 95 housed in individual vessels 98, 100 and 102 containing membrane modules where the gas contacts a gas contact side of membranes contained therein. Lines 104, 106 and 108 collect gas from 98, 100, and 102 respectively. Consumption of the gas by microorganisms in the modules reduces the volume of gas leaving the group of modules 95 relative to the volume of gas entering via line 90.

Line 110 delivers the remaining feed gas from the group of modules 95 to the group of modules 112. The modules in group 112 are identical in configuration to the modules contained in group 95, but group 112 only consists of two vessels 114 and 116. Lines 118 and 120 divide the remaining feed gas equally between the vessels. By reducing the number of vessels in group 112 the overall volumetric flow rate of gas through the individual modules and vessels remains approximately the same as that passing through individual modules in group 95. As a result the gas velocity through the individual modules and vessels varies by no more than about 20% between groups 95 and 112. Preferably the gas velocity through individual modules or vessels will vary by no more than 10%.

Lines 122 and 124 collect the remaining feed gas from vessels 114 and 116 and deliver it to a vessel 126 via a line 128. Vessel 126 houses a group of modules 130. The modules in group 130 are identical in configuration to the modules contained in groups 95 and 112, but group 130 only consists only of vessel 126. The further reduction to one vessel in group 130 keeps the overall volumetric flow rate of gas through the individual modules and vessel approximately the same as that passing through individual modules in groups 95 and 112, such that the resulting gas velocity through the individual modules and vessels varies by no more than about 20% from that in groups 95 and 112. Any remaining gas leaves vessel 126 via a line 132.

In FIG. 9 a liquid stream passes in parallel flow through all of the modules in groups 95, 112, and 130. A pump 136 delivers liquid from a tank 134 to an input header 138. Input header 138 delivers the liquid to input branches 142, 144, 146, 148, 150 and 152 in equal amounts and each branch delivers the liquid to vessels 126, 116, 114, 102, 100, and 98 respectively. Output branches 156, 158, 160, 162, 164, and 166 collect effluent liquid containing liquid products from vessels 98, 100, 102, 114, 116, and 126, respectively for collection into header 154.

Line 170 transports a portion of the effluent liquid to product recovery for the separation of liquid products. The product recovery section produces a product stream comprising the desired liquid product and a product deficient stream that returns to the tank 134 via line 172.

The rest of the effluent liquid from line 154 gets recycled to the vessels. Line 168 delivers the remainder of the effluent liquid to tank 134 for mixing with the product deficient stream 134 and any needed additives that enter the tank via line 174.

The arrangement of FIG. 9 lends itself equally well to use of hollow fiber membrane modules where the gas flow goes through the lumens of the fibers. In such a case the external piping remains the same as that shown in the FIG. 9, but internal chambers or manifolding delivers and collects the gas from the lumens of the fibers while liquid fills the volume of the vessels to surround the outside of the fibers with the process fluid.

Arrangements that circulate gas through the lumens of hollow fibers membranes may find better economy in the use of a large tank as single vessel to immerse the membrane modules in the process liquid. A closed tank can house a number of the membrane modules in a process liquid to achieve a very large total membrane surface area with a small number of membrane tanks thereby simplifying plant design and reducing costs. The membrane tank can take round, square, rectangular or any other suitable shape. In many applications the tank needs to provide a gas-tight environment, particularly for anaerobic operation. The membrane modules can be designed to provide a desired distribution of flow of the process liquid about individual hollow fibers and/or small bundles of hollow fibers. Those skilled in the art will appreciate that the membrane modules can have any cross section as desired for a particular purpose, such as round, rectangular, square, or any other cross section that accommodates a desired pitch and/or spacing.

The tank can also provide the means of temperature and pH controls for the circulating liquid, which contains nutrients needed to sustain the activity of the microbial cells. The liquid in the tank may be stirred to provide adequate mixing and sparged with a suitable gas, if necessary, to maintain a suitable gaseous environment. The superficial linear velocity of the liquid tangential to the membrane should be in the range of 0.01 to 20 cm/s, preferably 0.05 to 5 cm/s, and most preferably 0.2 to 1.0 cm/s. In addition to the liquid linear velocity, the biofilm thickness can be controlled by other means to create shear on the liquid-biofilm interface, including scouring of the external membrane surface with gas bubbles and free movement of the hollow fibers. Also, operating conditions that affect the metabolic activity of the microbial cells and the mass transfer rates of gases and nutrients can be manipulated to control the biofilm thickness. The biofilm thickness is typically in the range of 5-500 μm, preferably 5-200 μm.

Figure 10:
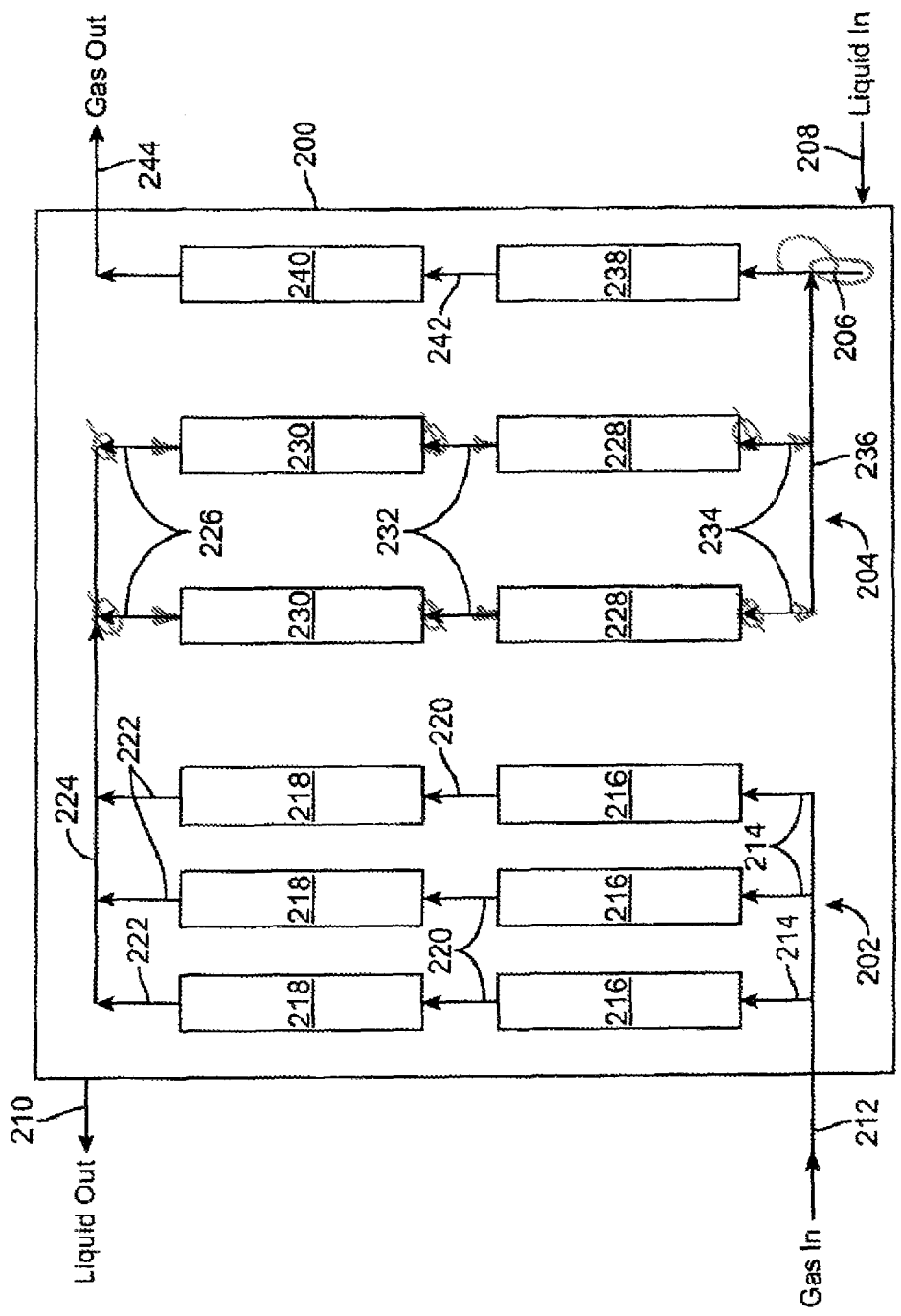
FIG. 10 schematically depicts groups of stacked modules surrounded by a liquid containment vessel.

FIG. 10 schematically shows an arrangement where a module tank 200 houses three groups of modules 202, 204, and 206. A process gas is disposed in the hollow fiber lumens and a biofilm is disposed on the outer surface of the hollow fibers of the modules. Process gas passes through the hollow fiber wall to interact with the biofilm and generate a liquid product that mixes with the process liquid. A seal between the contents of the module tank 200 and the ambient atmosphere, formed by the wall of the tank 200 and seals on inlet and outlet connections, maintains an anaerobic atmosphere within the tank 200. The process liquid circulates through the tank 200 from a liquid inlet 208 to a liquid outlet 210. Inlet 208 and outlet 210 can comprise part of a re-circulating liquid loop for keeping liquid moving through the tank. A portion of the liquid withdrawn from line 210 goes to product recovery to recover liquid products. All of the modules in the groups have open sides so that liquid surrounds all of the fibers in each module.

A gas inlet conduit 212 delivers the feed gas to module group 202 via pipe branches 214. Module group 202 consists of three stacks of modules with a bottom module 216 in the bottom of each stack, a top module 218 in the top of each stack and an interconnection conduit 220 for transferring gas from the bottom to the top module.

Pipe branches 222 collect gas from each top module 218 and transfer to module group 204 via line 224 and pipe branches 226. Module group 204 contains two stacks of modules with an upper module 230, a lower module 228 and an interconnection conduit 232 for transferring gas from the module 230 to module 228. Module group 204 contains one less stack of modules than group 202 to reduce the gas flow area of module group 204 relative to the gas flow area provided by module group 202.

A line 236 transfers the remaining feed gas from module group 204 to module group 206. The remaining feed gas passes via line 206 to a bottom module 238 and to an upper module 240 via an interconnection conduit 242. Once again the number of modules in group 206 is reduced relative to group 204 to reduce the gas flow area provided by the group 206 and thereby maintain a sufficiently high gas velocity through the lumens of modules 238 and 240 to prevent low flow conditions and resulting condensation. A gas outlet conduit 244 recovers any remaining feed gas from the module 240.

As the feed gas passes serially through the groups of modules consumption of the feed gas components may change the composition of the gas stream. For example when applying the process to the conversion of syngas comprising CO, CO2 and H2 into liquid products, the microorganism may consume more of the CO present in the gas stream leaving a greater proportion of CO2, H2 and any inert gas components as the stream passes through groups of modules. The concentration of various components in the gas stream can affect the productivity of certain microorganisms and the selectivity of the organisms toward making certain desired liquid products.

To overcome any negative conditioning of the microorganisms based on their relative positioning in a serial gas flow arrangement there can be benefits to rotating the position of the module groups with respect to the path of the gas flow. By sequentially alternating the gas delivery path all of the modules can periodically get grouped with different numbers of modules and receive the various different composition of feed gas as it changes along the gas flow path.

Figure 11:
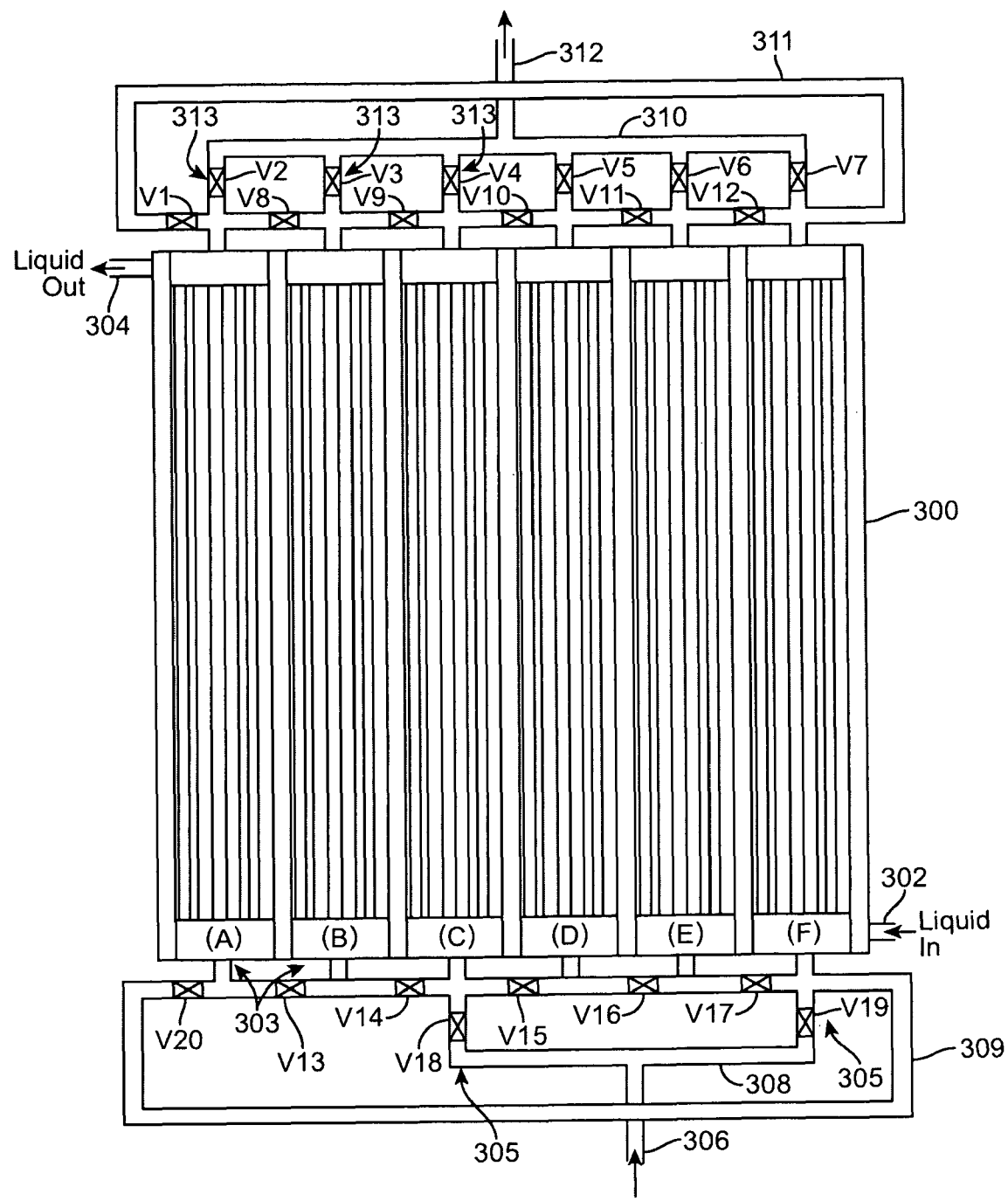
FIG. 11 schematically depicts a plurality of modules in a common vessel and a piping system with valves for controlling gas distribution to the modules.

FIG. 11 shows an arrangement where a single tank 300 circulates a process liquid from an inlet 302 across six modules A, B, C, D, E, and F to an outlet 304. Feed gas flows to the modules from an inlet line 306 through an inlet manifold 308. An inlet pipe loop 309 and individual module nozzles for each of modules A-F provide further delivery of feed gas and circulation of feed gas between modules by the operation of valves V13 through V20. To provide delivery and circulation of the gas feed modules A, B, D, and E each communicate with a "T" valve junction and modules C and F each communicate with a "cross" valve junction. In a similar manner individual module outlet nozzles collect fluid from modules A-F for withdrawal of feed gas and circulation of feed gas between modules. Each of the modules A-F communicate with "cross" valve junctions 313 that communicate with valves V1-V12 to regulate the circulation of the gas around outlet pipe loop 311, through outlet manifold 310 and into outlet header 312.

Table 2 indicates six different sequence position for the valve operation by which all of the modules serve periodically and successively in a group of three modules, a group of two modules and as a single module. Under the columns titled Module Grouping/Function a number appear under each Module letter. The number indicates for each particular sequence whether a particular module in a three, two, or one module group. To the left of the Module Grouping/Function column each valve number appears over a separate column. Below each valve number the condition of that valve for each particular sequence position appears. A "+" in the box indicates the valve is open and while a "−" indicates that the valve is closed. In all cases this particular valving arrangement will produce an upflow condition when the module operates in a group of three or as a single module or in a downflow condition when the module operates in a group of 2.

The valve and piping arrangement will permit a continuous cycling of the modules through all of the different grouping. In this manner the microorganism regularly experience the same changes in feed composition and the same changes, if any, in flow conditions. The time period for each sequence position can vary from 1 minute to 5 days and more preferably is in a time range of from 10 minutes to 8 hours.

A further modification of the module rotation and sequencing can incorporate a purge step to flush material from the colonies of microorganisms particularly when they reside within biopores on the gas side contact side of the membrane. A suitable purge step for clearing biopores may be effected by raising the pressure of the liquid phase or lowering the pressure of the gas sufficiently to have the difference in pressure cause liquid to permeate from the liquid side to the gas side of the membrane. Purging may last anywhere from 10 seconds to 10 minutes and take place on a frequency of from 24 to 1000 hours.

Figure 12:
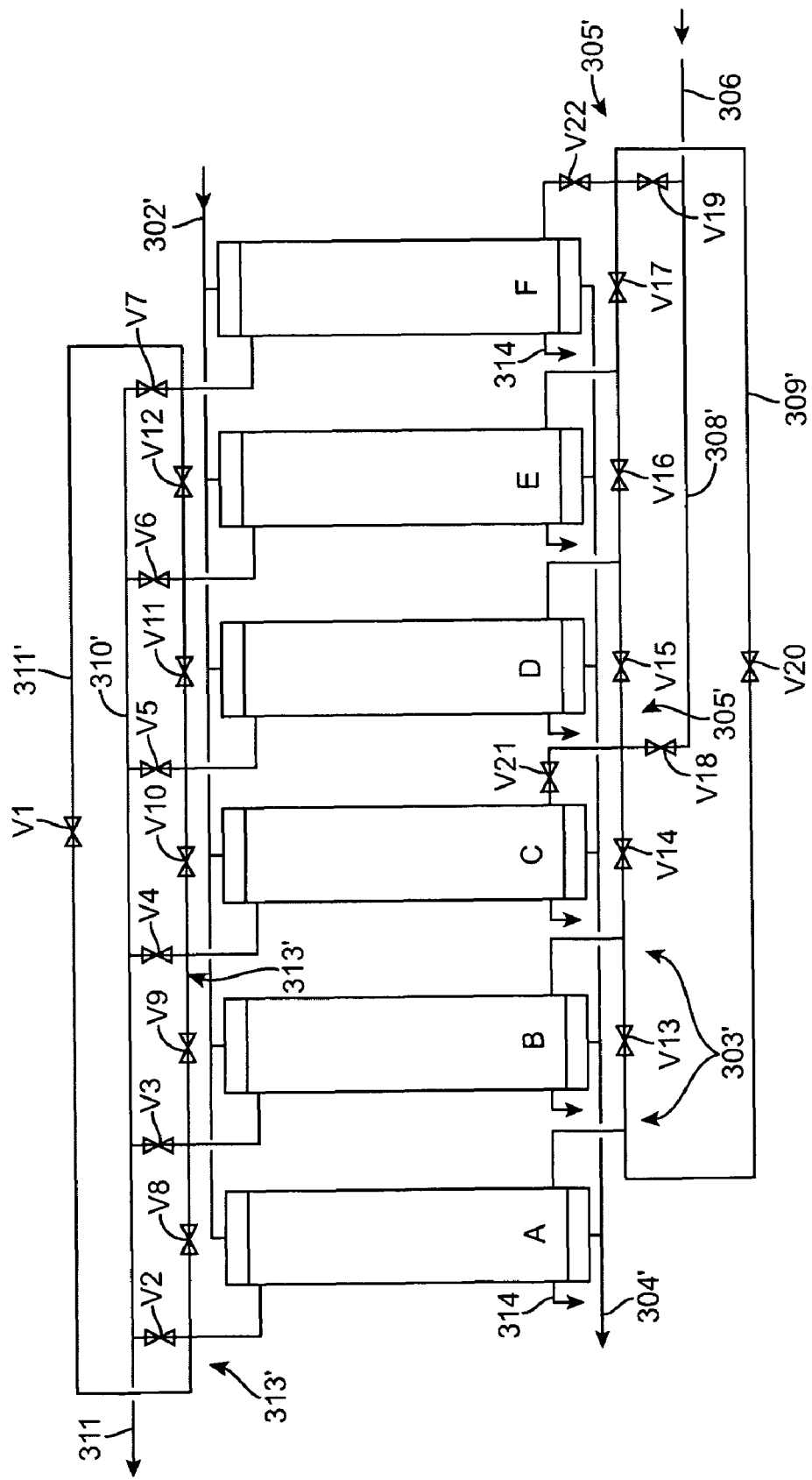
FIG. 12 schematically depicts a plurality of in individual vessels and a piping system for controlling gas distribution to the modules.

FIG. 12 schematically depicts a similar piping and valve arrangement to that depicted in FIG. 11. Although represented differently the number of modules sections remains the same in FIG. 11 to FIG. 12. The modules A-F also vary in function in that they are each enclosed by an individual vessel and the process liquid enter and leaves the lumens of membranes contained in each vessel separately via an inlet manifold arrangement 302' for distributing liquid individually to each of the modules and an outlet manifold arrangement 304' for collecting liquid individually from each of the modules.

FIG. 12 uses piping arrangements consisting of lines 308'-311' that function in the manner described in conjunction with FIG. 11. to distribute feed gas in the essentially the same manner as described for FIG. 11 except in this case the feed gas flows to the shell side of each vessel A-F. Another change in the valve arrangement from FIG. 11 to FIG. 12 is the addition of a valve V21 for module C and a valve V22 for module F. Valves V21 and V22 allow each module to undergo an individual purge step. The vessel surrounding each module also has an individual drain to remove fluid from the shell side of the module, primarily during the purge step. Apart from these changes, Table 3 indicates six different sequence positions for the valve operation by which all of the modules serve periodically and successively in a group of three modules, a group of two modules and as a single module. Under the columns titled Module Grouping/Function a number again appears under each Module letter. The number again indicates for each particular sequence whether a particular module is in a three, two, or one module group. To the left of the Module Grouping/Function column each valve number appears again over a separate column with the "+" or the "−" again indicating the condition of that valve for each particular sequence position appears. In all cases the particular valving arrangement will produce an upflow condition when the module operates in a group of three or as a single module or in a downflow condition when the module operates in a group of 2.

The columns under the Module Grouping/Function title now also include a designation 3P. This indicates when a particular module is undergoing the purge step. The purge step may last for all or only a portion of the time that a module remains in a particular sequence condition. The purge sequence for a module consists of temporarily stopping the flow of gas into and out of module. The module remains blocked from gas flow to reduce the gas pressure within the module to the point where process liquid flows across the membrane and onto the gas contacting surface of the membrane. Upon completion of the purge steps the gas valve for delivering and withdrawing feed gas are again opened and the module continues in its operational mode. Drain 314 normally remains closed except to drain accumulated liquid that collects at the bottom of the module which may be done during the purge step or at any time in the sequence.

The invention can sequence individual modules or group of modules. Application of this invention to commercial facilities may involve the use of hundreds of modules. In such application the individual valves will control large groups of modules to thereby minimize the required number of such valves. In fact each module section shown in FIG. 12 can actually represent a collection of modules.

Figure 13:
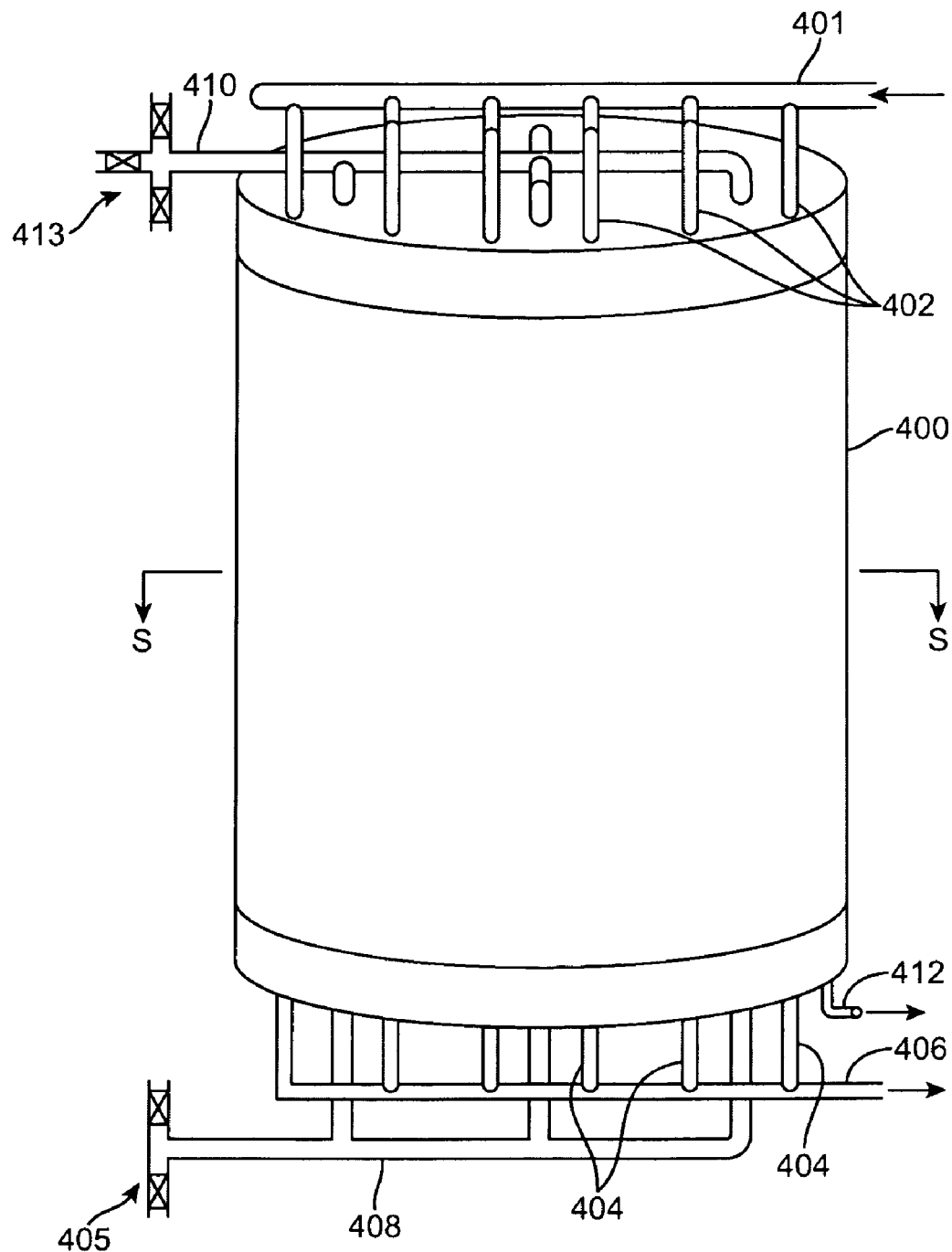
FIG. 13 depicts a vessel for retaining a group of modules as a single bank.
Figure 14:
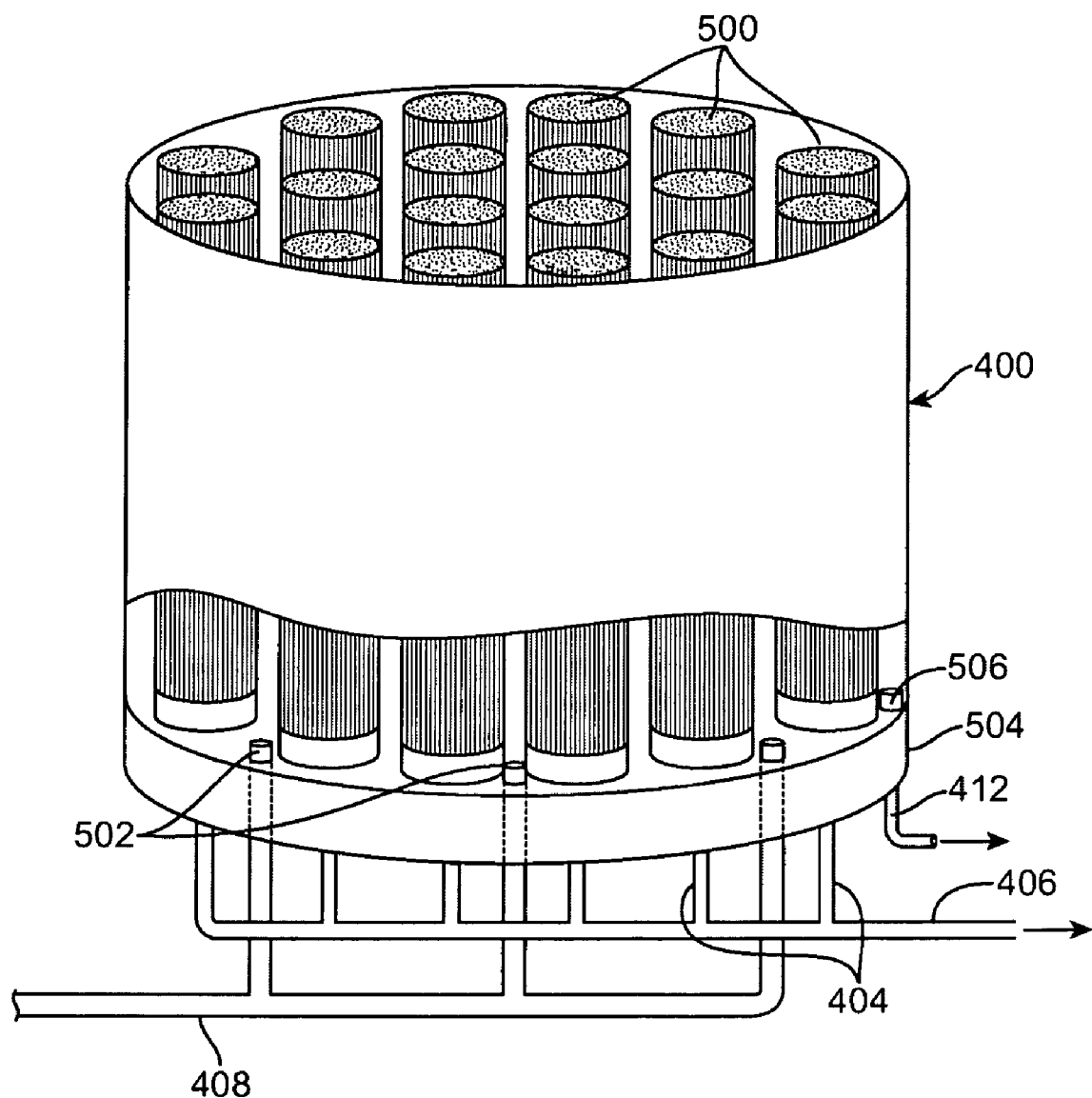
FIG. 14 is a section and cutaway view showing the modules in the bank of FIG. 13.

FIGS. 13 and 14 schematically depict an assemblage of multiple modules for control by the valve system of the types generally illustrated by FIGS. 11 and 12. In this module assemblage an inlet header 401 having branch lines 402 supplies liquid to a plurality of modules housed in a vessel 400. A series of branch lines 404 collect liquid from the bottom of the modules and deliver the liquid to an outlet header 406. In practice, vessel 400 serves as one element that together with additional like vessels make up collections of module elements for grouping as required for this invention.

Therefore, to reduce the piping and valves that are required for operating with large numbers of modules the assemblage depicted in FIG. 13 can receive gas flow from a single line and exhaust gas from a single line. In effect each individually controlled module A-F in FIG. 12 can be substituted with an assembly of modules as shown in FIG. 12 and integrated into a pipe identical with each "cross" valve junction 413 and/or a "T" valve junction 405. Each valve junction communicates gas to the open area of the vessel through a series of ports connected to a lower piping network 408 or an upper piping network 410. With the valve arrangement of FIG. 12 applied to six vessels of the type shown in FIG. 13 the same number of valves can regulate flow for a very large grouping of modules in the same manner described in relation to Table 3. The operation can include a purge step for which the vessel incorporates a drain nozzle 412 to remove liquid.

FIG. 14 depicts additional details of the module and piping arrangement within and about the vessel 400 through a section taken along line S-S in FIG. 13 and partial cut-away view at the bottom of the vessel. Vessel 400 houses a plurality of individual modules. Each module is of the type shown in FIG. 7 having open sidewalls for communication of gas that enters or leaves the vessel through ports 502 that communicate the gas stream through bottom plate 504 and with piping network 408. Each 502 protrudes slightly from the top plate 504 to keep liquid from entering the pipe during the purge step. Port 506 collects liquid from inside vessel 400 for removal through drain nozzle 412.

If the vessel 400 operates at high pressure, it may incorporate a pressure balancing head (not shown) with appropriate geometry to more efficiently withstand the pressure load and reduce the required thickness of plate 504.

Liquid flows through downward through the lumens of the fibers in modules 500. Pipe branches 404 each communicate via a sealed connection with a collection chamber of the type shown by reference number 36 in FIG. 7. Outlet header 408 collects the liquid for separation of liquid products from the liquid stream by passage to a separation section either directly or via flow through additional groups of modules.

Accordingly this invention can find broad application to controlling groups of modules to effect a variety of operating applications. In addition to the purge and grouping function as explained herein the process of this invention may include additional operational steps such as initial and periodic inoculation of cultures onto the membrane surfaces. The language of the following claims is not intended to exclude their coverage from any such variations and modifications in the application of this invention.

TABLE 2

The valve and piping arrangement for continuous cycling of modules in FIG. 11.

| Sequence Position | Module Grouping/Function | | | | | | Valve Condition | | | | | | | | | | | | | | | | | | | |
|---|---|---|---|---|---|---|---|---|---|---|---|---|---|---|---|---|---|---|---|---|---|---|---|---|---|---|
| | A | B | C | D | E | F | V1 | V2 | V3 | V4 | V5 | V6 | V7 | V8 | V9 | V10 | V11 | V12 | V13 | V14 | V15 | V-16 | V-17 | V-18 | V-19 | V-20 |
| 1 | 3 | 3 | 3 | 2 | 2 | 1 | − | − | − | − | − | − | + | + | + | + | + | − | + | + | − | + | + | + | − | − |
| 2 | 3 | 3 | 2 | 2 | 1 | 3 | + | − | − | − | − | + | − | + | + | + | − | − | + | − | + | + | − | − | + | + |
| 3 | 3 | 2 | 2 | 1 | 3 | 3 | + | − | − | + | − | − | + | + | − | − | + | − | + | + | − | + | − | + | + |
| 4 | 2 | 2 | 1 | 3 | 3 | 3 | + | − | − | + | − | − | + | − | − | + | + | + | + | − | + | + | − | + | − |
| 5 | 2 | 1 | 3 | 3 | 3 | 2 | + | − | + | − | − | − | − | − | + | + | + | + | − | + | + | − | + | − | + |
| 6 | 1 | 3 | 3 | 3 | 2 | 2 | − | + | − | − | − | − | − | − | + | + | + | − | + | + | − | + | + | − | + |

TABLE 3

The valve and piping arrangements for continuous cycling and periodical purging of modules in FIG. 12.

| Sequence Position | Module Grouping/Function | | | | | | Valve Condition | | | | | | | | | | | | | | | | | | | | |
|---|---|---|---|---|---|---|---|---|---|---|---|---|---|---|---|---|---|---|---|---|---|---|---|---|---|---|---|
| | A | B | C | D | E | F | V1 | V2 | V3 | V4 | V5 | V6 | V7 | V8 | V9 | V10 | V11 | V-12 | V-13 | V-14 | V-15 | V-16 | V-17 | V-18 | V-19 | V-20 | V-21 | V-22 |
| 1 | 1 | 3P | 3 | 3 | 2 | 2 | − | + | − | − | − | − | − | − | P | + | + | + | − | P | + | − | + | + | − | + | + | + |
| 2 | 2 | 1 | 3P | 3 | 3 | 2 | + | − | + | − | − | − | − | − | − | P | + | + | + | − | + | + | − | + | − | + | P | + |
| 3 | 2 | 2 | 1 | 3P | 3 | 3 | + | − | − | + | − | − | − | + | − | − | P | + | + | + | − | P | + | − | + | − | + | + |
| 4 | 3 | 2 | 2 | 1 | 3P | 3 | + | − | − | − | + | − | − | + | + | − | − | P | − | + | + | − | P | − | + | + | + | + |
| 5 | 3 | 3 | 2 | 2 | 1 | 3P | P | − | − | − | − | + | − | + | + | + | − | − | + | − | + | + | − | − | + | + | + | P |
| 6 | 3P | 3 | 3 | 2 | 2 | 1 | − | − | − | − | − | − | + | P | + | + | + | − | P | + | − | + | + | − | − | + | + | + |

The invention claimed is:

1. A process for the production of a liquid product from a gas feed comprising at least one of CO, and CO2 and H2 by its partial consumption by microorganisms as it passes serially through groups of conversion modules to produce a liquid product comprising at least one of ethanol, butanol, hexanol, acetic acid, butyric acid, and combinations thereof, wherein the process comprises:
   a. passing a feed gas in parallel flow at a first volumetric rate and a first gas flow velocity to a first group of modules comprising membrane elements wherein each module defines a uniform gas flow area to collectively provide a first gas flow area for contacting the feed gas with a gas contact surface therein to convert a portion of the gas feed to a liquid product by contact with microorganisms;
   b. passing a first stream of liquid media to a first liquid contact surface defined by the membrane elements of said first group of modules to recover the liquid product from the liquid contact surface;
   c. recovering the remainder of feed gas from the first gas flow area as a first effluent gas;
   d. passing at least a portion of the first effluent gas at a second volumetric flow rate and a second gas flow velocity to a group of second modules comprising membrane elements wherein each module defines the same uniform gas flow area as each module in the first group of modules to collectively provide a second gas flow area for contacting the feed gas with a gas contact surface therein to convert an additional portion of the feed gas to the liquid product by contact with microorganisms wherein first group of modules contains more modules than the second group of modules, and the second volumetric rate is less than the first volumetric rate; and,
   e. passing a second stream of liquid media to a liquid contact surface defined by the membrane elements of said second group of modules to recover the liquid product from the second liquid contact surface.

2. The process of claim 1 wherein the first flow and second flow of liquid media remains directed to the same modules in the groups of first and second modules as the feed gas flow and first effluent gas flow periodically alternates to different modules in the group of first and second modules.

3. The process of claim 1 wherein the modules in the first and second group of modules comprise multiple banks of modules and each bank of modules receives gas from a common gas distribution point and delivers gas to a common gas collection point.

4. The process of claim 1 wherein the number of modules in the first group and the number of modules in the second group varies in proportion to the first volumetric rate and the second volumetric rate and the and the first gas flow velocity varies by no more than 30% from the second gas flow velocity.

5. The process of claim 1 wherein the first and second modules comprise hollow fiber membranes and the lumens of the hollow fiber membranes define the first and second gas flow areas.

6. The process of claim 4 wherein the remainder of the feed gas from the second group of modules passes to a third group of modules wherein each module defines the same uniform gas flow area as each module in the first group of modules to collectively provide a third gas flow area for contacting the feed gas with a gas contact surface therein to convert an additional portion of the feed gas to the liquid product.

7. The process of claim 1 wherein a portion of the modules in the first group of first modules periodically alternate with modules in the second group of modules by redirection of feed gas flow and first effluent gas flow to different modules.

8. The process of claim 7 wherein the membrane elements comprise hollow fibers, the gas contact surface is on the outside of the fibers, the lumens of the fibers provide the liquid contact surface, and a portion of the modules undergo periodic purging by increasing the relative pressure across the lumen to permeate water to the outside surface of the membrane.

9. The process of claim 1 wherein the gas contact surface retains a biolayer comprising the microorganisms that ingest at least one of CO, CO2 and H2 and the microorganisms express ethanol that comprises the liquid product.

10. A process for the production of a liquid product a comprising at least one of ethanol, butanol, hexanol, acetic acid, butyric acid, and combinations thereof from a gas feed comprising at least one of CO, and CO2 and H2 by its partial consumption as it passes in parallel through each module in individual groups of conversion modules and serially between groups of conversion modules wherein the conversion modules comprise membrane elements with each module defining a uniform gas flow area, a liquid contact surface and a gas contact surface that retains a biolayer of microorganisms and wherein the process comprises:
   a. passing a feed gas at a first volumetric rate and a first gas velocity to a first group of modules to collectively provide a first gas flow area and to convert a portion of the gas feed to a liquid product;
   b. passing a first stream of liquid media to a liquid contact surface defined by said first group of modules to recover the liquid product from the liquid contact surface;
   c. recovering the remainder of the feed gas from the first gas flow area;
   d. passing at least a portion of the feed gas recovered from the first gas flow area at a second volumetric flow rate and a second gas flow velocity to a group of second modules to collectively provide a second gas flow area for contacting the feed gas with a gas contact surface therein to convert an additional portion of the feed gas to the liquid product wherein the second group of modules contains less modules than the first group of modules and the second volumetric rate is less than the first volumetric rate;

e. passing a second stream of liquid media to a liquid contact surface defined by the membrane elements of said second group of modules to recover the liquid product from the second liquid contact surface;

f. recovering the remainder of the feed gas from the second gas flow area;

g. maintaining at least one module in a purge mode by permeating the liquid media from the liquid contact surface to the gas contact surface in the module in purge mode to flush microorganisms from the gas contact surface of the module in purge mode; and, h. sequentially changing the modules that are in the first group of modules with modules that are in the second group of modules and the module that is in purge mode so that periodically all of the modules undergo so that periodically all of the modules undergo receiving feed gas at the first volumetric rate and at the second volumetric rate and undergo purging.

11. The process of claim 10 wherein each of the modules receive the first stream and the second stream of liquid media as separate streams that flow parallel.

12. The process of claim 10 wherein the gas contact surface comprises the outer surface of hollow fiber membranes and the microorganisms express ethanol as the liquid product.

13. The process of claim 1 wherein the first and second liquid media flow in parallel flow through the modules as separate streams.

14. The process of claim 2 wherein the first and second liquid media flow in parallel flow through the modules as separate streams.

* * * * *